United States Patent
Warren et al.

(10) Patent No.: US 9,622,301 B2
(45) Date of Patent: Apr. 11, 2017

(54) SMOKE DETECTOR WITH REGULATED CONSTANT-CURRENT CIRCUIT FOR DRIVING OPTICAL SOURCES

(71) Applicant: Google Inc., Mountain View, CA (US)

(72) Inventors: Daniel Adam Warren, San Francisco, CA (US); Ian C. Smith, Mountain View, CA (US); Brian Jonathan Conner, San Jose, CA (US)

(73) Assignee: GOOGLE INC., Mountain View, CA (US)

( * ) Notice: Subject to any disclaimer, the term of this patent is extended or adjusted under 35 U.S.C. 154(b) by 146 days.

(21) Appl. No.: 14/717,739

(22) Filed: May 20, 2015

(65) Prior Publication Data

US 2016/0345394 A1    Nov. 24, 2016

(51) Int. Cl.
| | |
|---|---|
| *G08B 17/10* | (2006.01) |
| *H05B 33/08* | (2006.01) |
| *G01N 21/53* | (2006.01) |
| *G08B 17/107* | (2006.01) |

(52) U.S. Cl.
CPC ......... *H05B 33/0815* (2013.01); *G01N 21/53* (2013.01); *G08B 17/107* (2013.01); *H05B 33/0809* (2013.01); *H05B 33/0812* (2013.01); *G01N 2201/06153* (2013.01)

(58) Field of Classification Search
CPC ...... G08B 17/00; G08B 17/10; G08B 17/103; G08B 17/107; G08B 17/11; G08B 29/043; G01N 21/53; G01N 21/532
See application file for complete search history.

(56) References Cited

U.S. PATENT DOCUMENTS

| | | | | |
|---|---|---|---|---|
| 6,914,534 B2* | 7/2005 | Tanguay | ........... | G08B 5/38 340/286.05 |
| 2001/0038336 A1* | 11/2001 | Acevedo | ........... | G08B 7/06 340/628 |
| 2006/0192680 A1* | 8/2006 | Scuka | ........... | G08B 26/002 340/632 |
| 2010/0327766 A1* | 12/2010 | Recker | ........... | H02J 9/02 315/291 |
| 2013/0314225 A1* | 11/2013 | Baker | ........... | G08B 17/10 340/517 |
| 2015/0262464 A1* | 9/2015 | Goldenson | ........... | G08B 17/11 340/629 |

(Continued)

*Primary Examiner* — Jason M Crawford
(74) *Attorney, Agent, or Firm* — Van Court & Aldridge LLP

(57) ABSTRACT

Systems and methods for driving optical sources operating at different wavelengths within a smoke sensor are described herein. Multiple optical sources such as light emitting diodes may be used in a photoelectric smoke sensor to detect particles of different sizes. Photoelectric smoke sensors can operate by pulsing the LEDs and measuring a response in a light sensor. The signal measured at the light sensor changes based on the quantity of particles existing in a smoke chamber. Each optical source may have different operational characteristics and thus require different drive currents to operate. LED driving circuitry according to embodiments discussed herein provide a consistent and reliable drive current to each optical source, while maximizing efficiency of power consumption across a range of possible voltages provided by different power sources.

22 Claims, 6 Drawing Sheets

(56) References Cited

U.S. PATENT DOCUMENTS

2016/0019777 A1* 1/2016 Peterson ............... G08B 17/10
340/506
2016/0042638 A1* 2/2016 Sangha ............... G08B 29/043
340/628

* cited by examiner

SMOKE DETECTOR WITH REGULATED CONSTANT-CURRENT CIRCUIT FOR DRIVING OPTICAL SOURCES

TECHNICAL FIELD

This patent specification relates to systems and methods for power circuitry in hazard detection systems. More particularly, this specification relates to a smoke detector with regulated constant current circuitry driving optical sources operating at different wavelengths.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Hazard detection systems such as smoke detectors, carbon monoxide detectors, combination smoke and carbon monoxide detectors, as well as systems for detecting other dangerous conditions have been used in residential, commercial, and industrial settings for safety considerations.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Systems and methods for driving optical sources operating at different wavelengths within a smoke sensor are described herein. Multiple optical sources such as light emitting diodes may be used in a photoelectric smoke sensor to detect particles of different sizes. Photoelectric smoke sensors can operate by pulsing the LEDs and measuring a response in a light sensor. The signal measured at the light sensor changes based on the quantity of particles existing in a smoke chamber. Each optical source may have different operational characteristics and thus require different drive currents to operate. LED driving circuitry according to embodiments discussed herein provide a consistent and reliable drive current to each optical source, while maximizing efficiency of power consumption across a range of possible voltages provided by different power sources.

In one embodiment, a hazard detection system can include a smoke chamber having first and second light emitting diodes (LEDs), and a power input configured to receive a power signal ranging between first and second values. The system can include first LED driving circuitry coupled to receive the power signal from the power input and operative to provide a first LED power signal to the first LED, the first LED power signal characterized as having a value lower than the first and second values and a first substantially constant current value. The system can include second LED driving circuitry coupled to receive the power signal from the power input and operative to provide a second LED power signal to the second LED, the second LED power signal characterized as having a value higher than the first and second values and a second substantially constant current.

A method for communicating messages among devices of a fabric network is provided. The method can include managing, for a received message, a plurality of variables, the plurality of variables comprising a counter, a rebroadcast time period, a rebroadcasting decision point, and a first timer, wherein the rebroadcasting decision point exists within the rebroadcast time period, and wherein the first timer is reset at a beginning of the rebroadcast time period. The method includes determining when the first timer is equal to the rebroadcasting decision point, and rebroadcasting the received message if the counter is determined to be less than a threshold when the first timer is determined to be equal to the rebroadcasting decision point.

In another embodiment, a method for powering first and second light emitting diodes (LEDs) in a smoke sensor of a hazard detection system is provided. The system can include a power source signal ranging between a first signal value and a second signal value. The method can include managing a first LED power signal for use by the first LED by down converting the power source signal to the first LED power level, wherein the first LED power signal has a value less than the first and second signal values. The method can include managing a second LED power signal for use by the second LED by up converting the power source signal to the second LED power signal, wherein the second LED power signal has a value greater than the first and second signal values.

In another embodiment, a particle detector for use in a hazard detection system that is powered by one of a plurality of different power sources is provided. The power signal supplied by the plurality of power source can range between first and second values. The particle detector can include a particle detection chamber comprising an infrared light emitting diode (IR LED), a blue light emitting diode (LED), and a photodetector, a power input for receiving the power signal, and LED driving circuitry coupled to the IR LED, the blue LED, and to receive the power signal, the LED driving circuitry operative to supply a first drive current to the IR LED and a second drive current to the blue LED, wherein the first and second drive currents are independently derived from the power signal using independently operating low dropout regulators.

Various refinements of the features noted above may be used in relation to various aspects of the present disclosure. Further features may also be incorporated in these various aspects as well. These refinements and additional features may be used individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

A further understanding of the nature and advantages of the embodiments discussed herein may be realized by reference to the remaining portions of the specification and the drawings.

DETAILED DESCRIPTION OF THE DISCLOSURE

Figure 1:
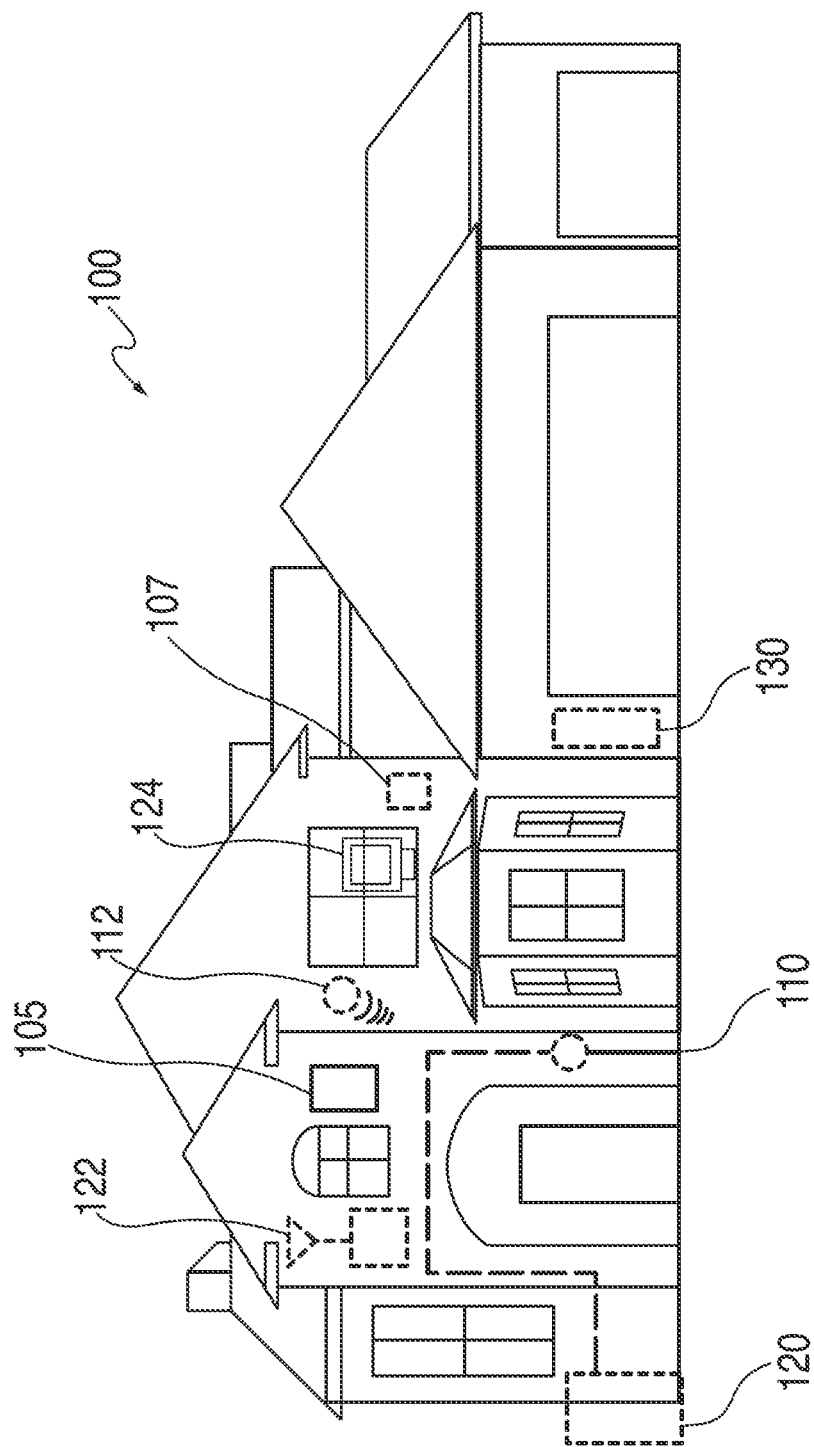
FIG. 1 is a diagram of an enclosure with a hazard detection system, according to some embodiments.

In the following detailed description, for purposes of explanation, numerous specific details are set forth to provide a thorough understanding of the various embodiments. Those of ordinary skill in the art will realize that these various embodiments are illustrative only and are not intended to be limiting in any way. Other embodiments will readily suggest themselves to such skilled persons having the benefit of this disclosure.

In addition, for clarity purposes, not all of the routine features of the embodiments described herein are shown or described. One of ordinary skill in the art would readily appreciate that in the development of any such actual embodiment, numerous embodiment-specific decisions may be required to achieve specific design objectives. These design objectives will vary from one embodiment to another and from one developer to another. Moreover, it will be appreciated that such a development effort might be complex and time-consuming but would nevertheless be a routine engineering undertaking for those of ordinary skill in the art having the benefit of this disclosure.

It is to be appreciated that while one or more hazard detection embodiments are described further herein in the context of being used in a residential home, such as a single-family residential home, the scope of the present teachings is not so limited. More generally, hazard detection systems are applicable to a wide variety of enclosures such as, for example, duplexes, townhomes, multi-unit apartment buildings, hotels, retail stores, office buildings, and industrial buildings. Further, it is understood that while the terms user, customer, installer, homeowner, occupant, guest, tenant, landlord, repair person, and the like may be used to refer to the person or persons who are interacting with the hazard detector in the context of one or more scenarios described herein, these references are by no means to be considered as limiting the scope of the present teachings with respect to the person or persons who are performing such actions.

Smoke detectors generally work according to an ionization technique or a light scattering technique. Conventional ionization techniques use a radioactive source to ionize air within the smoke chamber. The radioactive source is typically Americium-241 and can convert air molecules into positive and negative ions. In a conventional radioactive ionization smoke detector, a small amount of radioactive material may be placed between two electrically charged plates. The radiation emitting from the radioactive material ionizes the air between the plates and causes a current to flow between the plates. When smoke enters the smoke chamber, it disrupts ionization of the air, thereby reducing the current flow. Particularly, the ions may bond with the smoke or be displaced by the smoke, thus breaking the current flow between the two plates. When this reduced current flow is detected, an alarm may be activated. In conventional ionization smoke detectors, the radioactive source serves as the ionization source. Use of radioactive materials, however, is not desired, and some jurisdictions outlaw their use in commercial products such as smoke detectors.

The light scattering technique may be used in a photoelectric smoke alarm. In a photoelectric smoke alarm, a light source is aimed into a sensing chamber at an angle away from a sensor. Smoke enters the chamber, scatting light onto the light sensor, thereby triggering the alarm. Embodiments discussed herein operate in connection with a smoke chamber containing at least two optical sources, each operating at a different wavelengths (e g, infrared and blue), that project light energy into the chamber. One or more sensors can monitor for scattered light when smoke and other particles enter the chamber. Multiple optical sources may be used so that different sized particles can be detected, thereby enabling various algorithms to use the data to make more informed decisions when operating the hazard detection system. For example, white/gray smoke may have different mean particle sizes than black smoke. In addition, moisture particles may have different mean particles size than smoke particles and dust.

The optical sources are typically light emitting diodes (LEDS) that emit light energy when power is applied. For example, a blue LED may emit light energy in the blue electromagnetic spectrum and an infrared LED may emit light energy in the infrared electromagnetic spectrum. Different LEDs may exhibit different forward voltage drops based on a combination of factors such as semiconductor physics, output current, temperature, and manufacturing variances. For example, an IR LED may have a first voltage drop of about 2.1 volts and a blue LED may have a second voltage drop of about 3.4 volts. The different forward voltage drops may require the supply of different voltages within the system in order to adequately power the LEDs. In addition, in order for the LEDs to produce consistent light output, so that consistent and reliable smoke readings may be taken, the LEDs are each supplied with a substantially constant current using circuitry according to various embodiments described herein. Moreover, the circuitry is able to drive all the LEDs from a common power source with high efficiency even though the voltages provided by the common power source range from a first voltage to a second voltage, depending on the ultimate source of power (e.g., batteries, line power converted to DC, or USB power).

FIG. 1 is a diagram illustrating an exemplary enclosure 100 using hazard detection system 105, remote hazard detection system 107, thermostat 110, remote thermostat 112, heating, cooling, and ventilation (HVAC) system 120, router 122, computer 124, and central panel 130 in accordance with some embodiments. Enclosure 100 can be, for example, a single-family dwelling, a duplex, an apartment within an apartment building, a warehouse, or a commercial structure such as an office or retail store. Hazard detection system 105 can be battery powered, line powered, or line powered with a battery backup. Hazard detection system 105 can include one or more processors, multiple sensors, non-volatile storage, and other circuitry to provide desired safety monitoring and user interface features. Some user interface features may only be available in line powered embodiments due to physical limitations and power constraints. In addition, some features common to both line and battery powered embodiments may be implemented differently. Hazard detection system 105 can include the following components: low power wireless personal area network (6LoWPAN) circuitry, a system processor, a safety processor, non-volatile memory (e.g., Flash), WiFi circuitry, an ambient light sensor (ALS), a smoke sensor, a carbon monoxide (CO) sensor, a temperature sensor, a humidity sensor, a noise sensor, one or more ultrasonic sensors, a passive infra-red (PIR) sensor, a speaker, one or more light emitting diodes (LED's), and an alarm buzzer.

Hazard detection system 105 can monitor environmental conditions associated with enclosure 100 and alarm occupants when an environmental condition exceeds a predetermined threshold. The monitored conditions can include, for example, smoke, heat, humidity, carbon monoxide, radon, methane and other gasses. In addition to monitoring the safety of the environment, hazard detection system 105 can provide several user interface features not found in conventional alarm systems. These user interface features can include, for example, vocal alarms, voice setup instructions, cloud communications (e.g. push monitored data to the cloud, or push notifications to a mobile telephone, or receive software updates from the cloud), device-to-device communications (e.g., communicate with other hazard detection systems in the enclosure), visual safety indicators (e.g., display of a green light indicates it is safe and display of a red light indicates danger), tactile and non-tactile input command processing, and software updates.

Hazard detection system 105 can monitor other conditions that not necessarily tied to hazards, per se, but can be configured to perform a security role. In the security role, system 105 may monitor occupancy (using a motion detector), ambient light, sound, remote conditions provided by remote sensors (door sensors, window sensors, and/or motion sensors). In some embodiments, system 105 can perform both hazard safety and security roles, and in other embodiments, system 105 may perform one of a hazard safety role and a security role.

Hazard detection system 105 can implement multi-criteria state machines according to various embodiments described herein to provide advanced hazard detection and advanced user interface features such as pre-alarms. In addition, the multi-criteria state machines can manage alarming states and pre-alarming states and can include one or more sensor state machines that can control the alarming states and one or more system state machines that control the pre-alarming states. Each state machine can transition among any one of its states based on sensor data values, hush events, and transition conditions. The transition conditions can define how a state machine transitions from one state to another, and ultimately, how hazard detection system 105 operates. Hazard detection system 105 can use a dual processor arrangement to execute the multi-criteria state machines according to various embodiments. The dual processor arrangement may enable hazard detection system 105 to manage the alarming and pre-alarming states in a manner that uses minimal power while simultaneously providing failsafe hazard detection and alarming functionalities. Additional details of the various embodiments of hazard detection system 105 are discussed below.

Enclosure 100 can include any number of hazard detection systems. For example, as shown, hazard detection system 107 is another hazard detection system, which may be similar to system 105. In one embodiment, both systems 105 and 107 can be battery powered systems. In another embodiment, system 105 may be line powered, and system 107 may be battery powered. Moreover, a hazard detection system can be installed outside of enclosure 100.

Thermostat 110 can be one of several thermostats that may control HVAC system 120. Thermostat 110 can be referred to as the "primary" thermostat because it may be electrically connected to actuate all or part of an HVAC system, by virtue of an electrical connection to HVAC control wires (e.g. W, G, Y, etc.) leading to HVAC system 120. Thermostat 110 can include one or more sensors to gather data from the environment associated with enclosure 100. For example, a sensor may be used to detect occupancy, temperature, light and other environmental conditions within enclosure 100. Remote thermostat 112 can be referred to as an "auxiliary" thermostat because it may not be electrically connected to actuate HVAC system 120, but it too may include one or more sensors to gather data from the environment associated with enclosure 100 and can transmit data to thermostat 110 via a wired or wireless link. For example, thermostat 112 can wirelessly communicate with and cooperates with thermostat 110 for improved control of HVAC system 120. Thermostat 112 can provide additional temperature data indicative of its location within enclosure 100, provide additional occupancy information, or provide another user interface for the user (e.g., to adjust a temperature setpoint).

Hazard detection systems 105 and 107 can communicate with thermostat 110 or thermostat 112 via a wired or wireless link. For example, hazard detection system 105 can wirelessly transmit its monitored data (e.g., temperature and occupancy detection data) to thermostat 110 so that it is provided with additional data to make better informed decisions in controlling HVAC system 120. Moreover, in some embodiments, data may be transmitted from one or more of thermostats 110 and 112 to one or more of hazard detections systems 105 and 107 via a wired or wireless link (e.g., the fabric network).

Central panel 130 can be part of a security system or other master control system of enclosure 100. For example, central panel 130 may be a security system that may monitor windows and doors for break-ins, and monitor data provided by motion sensors. In some embodiments, central panel 130 can also communicate with one or more of thermostats 110 and 112 and hazard detection systems 105 and 107. Central panel 130 may perform these communications via wired link, wireless link (e.g., the fabric network), or a combination thereof. For example, if smoke is detected by hazard detection system 105, central panel 130 can be alerted to the presence of smoke and make the appropriate notification, such as displaying an indicator that a particular zone within enclosure 100 is experiencing a hazard condition.

Enclosure 100 may further include a private network accessible both wirelessly and through wired connections and may also be referred to as a Local Area Network or LAN. Network devices on the private network can include hazard detection systems 105 and 107, thermostats 110 and 112, computer 124, and central panel 130. In one embodiment, the private network is implemented using router 122, which can provide routing, wireless access point functionality, firewall and multiple wired connection ports for connecting to various wired network devices, such as computer 124. Wireless communications between router 122 and networked devices can be performed using an 802.11 protocol. Router 122 can further provide network devices access to a public network, such as the Internet or the Cloud, through a cable-modem, DSL modem and an Internet service provider or provider of other public network services.

Public networks like the Internet are sometimes referred to as a Wide-Area Network or WAN.

Access to the Internet, for example, may enable networked devices such as system 105 or thermostat 110 to communicate with a device or server remote to enclosure 100. The remote server or remote device can host an account management program that manages various networked devices contained within enclosure 100. For example, in the context of hazard detection systems according to embodiments discussed herein, system 105 can periodically upload data to the remote server via router 122. In addition, if a hazard event is detected, the remote server or remote device can be notified of the event after system 105 communicates the notice via router 122. Similarly, system 105 can receive data (e.g., commands or software updates) from the account management program via router 122.

Hazard detection system 105 can operate in one of several different power consumption modes. Each mode can be characterized by the features performed by system 105 and the configuration of system 105 to consume different amounts of power. Each power consumption mode corresponds to a quantity of power consumed by hazard detection system 105, and the quantity of power consumed can range from a lowest quantity to a highest quantity. One of the power consumption modes corresponds to the lowest quantity of power consumption, and another power consumption mode corresponds to the highest quantity of power consumption, and all other power consumption modes fall somewhere between the lowest and the highest quantities of power consumption. Examples of power consumption modes can include an Idle mode, a Log Update mode, a Software Update mode, an Alarm mode, a Pre-Alarm mode, a Hush mode, and a Night Light mode. These power consumption modes are merely illustrative and are not meant to be limiting. Additional or fewer power consumption modes may exist. Moreover, any definitional characterization of the different modes described herein is not meant to be all inclusive, but rather, is meant to provide a general context of each mode.

Although one or more states of the sensor state machines and system state machines may be implemented in one or more of the power consumption modes, the power consumption modes and states may be different. For example, the power consumption mode nomenclature is used in connection with various power budgeting systems and methods that are explained in more detail in U.S. Provisional Application Nos. 61/847,905 and 61/847,916.

Figure 2:
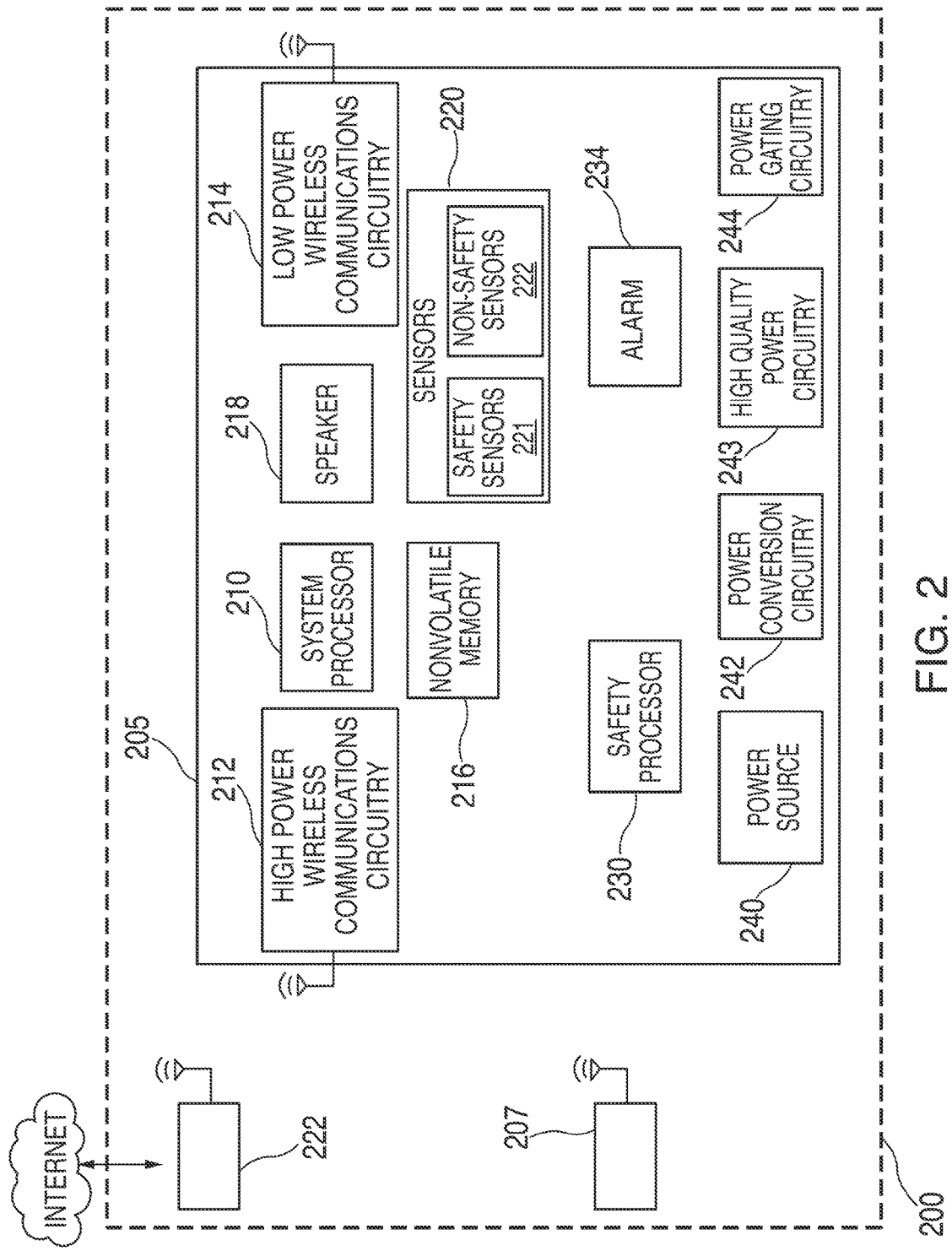
FIG. 2 shows an illustrative block diagram of a hazard detection system being used in an illustrative enclosure, according to some embodiments.

FIG. 2 shows an illustrative block diagram of hazard detection system 205 being used in an illustrative enclosure 200 in accordance with some embodiments. FIG. 2 also shows optional hazard detection system 207 and router 222. Hazard detection systems 205 and 207 can be similar to hazard detection systems 105 and 107 in FIG. 1, enclosure 200 can be similar to enclosure 100 in FIG. 1, and router 222 can be similar to router 122 in FIG. 1. Hazard detection system 205 can include several components, including system processor 210, high-power wireless communications circuitry 212 and antenna, low-power wireless communications circuitry 214 and antenna, non-volatile memory 216, speaker 218, sensors 220, which can include one or more safety sensors 221 and one or more non-safety sensors 222, safety processor 230, alarm 234, power source 240, power conversion circuitry 242, high quality power circuitry 243, and power gating circuitry 244. Hazard detection system 205 may be operative to provide failsafe safety detection features and user interface features using circuit topology and power budgeting methods that may minimize power consumption.

Hazard detection system 205 can use a bifurcated processor circuit topology for handling the features of system 205. Both system processor 210 and safety processor 230 can exist on the same circuit board within system 205, but perform different tasks. System processor 210 is a larger more capable processor that can consume more power than safety processor 230. System processor 210 can be operative to process user interface features. For example, processor 210 can direct wireless data traffic on both high and low power wireless communications circuitries 212 and 214, access non-volatile memory 216, communicate with processor 230, and cause audio to be emitted from speaker 218. As another example, processor 210 can monitor data acquired by one or more sensors 220 to determine whether any actions need to be taken (e.g., shut off a blaring alarm in response to a user detected action to hush the alarm).

Safety processor 230 can be operative to handle safety related tasks of system 205. Safety processor 230 can poll one or more of sensors 220 and activate alarm 234 when one or more of sensors 220 indicate a hazard event is detected. Processor 230 can operate independently of processor 210 and can activate alarm 234 regardless of what state processor 210 is in. For example, if processor 210 is performing an active function (e.g., performing a WiFi update) or is shut down due to power constraints, processor 230 can activate alarm 234 when a hazard event is detected. In some embodiments, the software running on processor 230 may be permanently fixed and may never be updated via a software or firmware update after system 205 leaves the factory. In other embodiments, processor 230 may be updated when system 205 is in the field.

Compared to processor 210, processor 230 is a less power consuming processor. Thus by using processor 230 in lieu of processor 210 to monitor a subset of sensors 220 yields a power savings. If processor 210 were to constantly monitor sensors 220, the power savings may not be realized. In addition to the power savings realized by using processor 230 for monitoring the subset of sensors 220, bifurcating the processors also ensures that the safety monitoring and core alarming features of system 205 will operate regardless of whether processor 210 is functioning. By way of example and not by way of limitation, system processor 210 can include a relatively high-powered processor such as Freescale Semiconductor K60 Microcontroller, while safety processor 230 may comprise a relatively low-powered processor such as a Freescale Semiconductor KL16 Microcontroller. Overall operation of hazard detection system 205 entails a judiciously architected cooperation of system processor 210 and safety processor 230, with system processor 210 performing selected higher-level, advanced functions that may not have been conventionally associated with hazard detection units (for example: more advanced user interface and communications functions; various computationally-intensive algorithms to sense patterns in user behavior or patterns in ambient conditions; algorithms for governing, for example, the brightness of an LED night light as a function of ambient brightness levels; algorithms for governing, for example, the sound level of an onboard speaker for home intercom functionality; algorithms for governing, for example, the issuance of voice commands to users; algorithms for uploading logged data to a central server; algorithms for establishing network membership; and so forth), and with safety processor 230 performing the more basic functions that may have been more conventionally associated with hazard detection units (e.g., smoke and CO monitoring, actuation of shrieking/buzzer alarms upon alarm detection). By way of example and not by way of limitation, system processor 210 may consume on the order of 18 mW when it is in a relatively high-power active state and performing one or more of its assigned advanced functionalities, whereas safety processor 230 may only consume on the order of 0.05 mW when it is performing its basic monitoring functionalities. However, again by way of example and not by way of limitation, system processor 210 may consume only on the order of 0.005 mW when in a relatively low-power inactive state, and the advanced functions that it performs are judiciously selected and timed such the system processor is in the relatively high power active state only about 0.05% of the time, and spends the rest of the time in the relatively low-power inactive state. Safety processor 230, while only requiring an average power draw of 0.05 mW when it is performing its basic monitoring functionalities, should of course be performing its basic monitoring functionalities 100% of the time. According to one or more embodiments, the judiciously architected functional overlay of system processor 210 and safety processor 230 is designed such that hazard detection system 205 can perform basic monitoring and shriek/buzzer alarming for hazard conditions even in the event that system processor 210 is inactivated or incapacitated, by virtue of the ongoing operation of safety processor 230. Therefore, while system processor 210 is configured and programmed to provide many different capabilities for making hazard detection unit 205 an appealing, desirable, updatable, easy-to-use, intelligent, network-connected sensing and communications node for enhancing the smart-home environment, its functionalities are advantageously provided in the sense of an overlay or adjunct to the core safety operations governed by safety processor 230, such that even in the event there are operational issues or problems with system processor 210 and its advanced functionalities, the underlying safety-related purpose and functionality of hazard detector 205 by virtue of the operation of safety processor 230 will continue on, with or without system processor 210 and its advanced functionalities.

High power wireless communications circuitry 212 can be, for example, a Wi-Fi module capable of communicating according to any of the 802.11 protocols. For example, circuitry 212 may be implemented using WiFi part number BCM43362, available from Murata. Depending on an operating mode of system 205, circuitry 212 can operate in a low power "sleep" state or a high power "active" state. For example, when system 205 is in an Idle mode, circuitry 212 can be in the "sleep" state. When system 205 is in a non-Idle mode such as a Wi-Fi update mode, software update mode, or alarm mode, circuitry 212 can be in an "active" state. For example, when system 205 is in an active alarm mode, high power circuitry 212 may communicate with router 222 so that a message can be sent to a remote server or device.

Low power wireless communications circuitry 214 can be a low power Wireless Personal Area Network (6LoWPAN) module or a ZigBee module capable of communicating according to a 802.15.4 protocol. In some embodiments, low power wireless communications circuitry 214 may serve as a node in a fabric network of devices. In another embodiment, circuitry 214 can be part number EM357 SoC available from Silicon Laboratories. In some embodiments, circuitry 214 can include Bluetooth Low Energy circuitry. Depending on the operating mode of system 205, circuitry 214 can operate in a relatively low power "sleep" state or a relatively high power "awake" state. When system 205 is in the Idle mode, WiFi update mode, or software update mode, circuitry 214 can be in the "sleep" state. Circuitry 214 may transition from the sleep state to the awake state in response to receipt of a wake packet (transmitted by another device) or in response to a state change in one of the state machines running on system 205. When system 205 is in the Alarm mode, circuitry 214 can transmit fabric messages so that the low power wireless communications circuitry in system 207 can receive data indicating that system 205 is alarming. Thus, even though it is possible for high power wireless communications circuitry 212 to be used for listening for alarm events, it can be more power efficient to use low power circuitry 214 for this purpose. Power savings may be further realized when several hazard detection systems or other systems having low power circuitry 214 form an interconnected wireless fabric network.

Power savings may also be realized because in order for low power circuitry 214 to continually listen for data transmitted from other low power circuitry, circuitry 214 may constantly be operating in its "sleep" state. This state consumes power, and although it may consume more power than high power circuitry 212 operating in its sleep state, the power saved versus having to periodically activate high power circuitry 214 can be substantial. When high power circuitry 212 is in its active state and low power circuitry 214 is in its awake state, high power circuitry 212 can consume substantially more power than low power circuitry 214.

In some embodiments, low power wireless communications circuitry 214 can be characterized by its relatively low power consumption and its ability to wirelessly communicate according to a first protocol characterized by relatively low data rates, and high power wireless communications circuitry 212 can be characterized by its relatively high power consumption and its ability to wirelessly communicate according to a second protocol characterized by relatively high data rates.

In some embodiments, low power wireless communications circuitry 214 may be a mesh network compatible module that does not require a distinguished access point in order to communicate to devices in a network. Mesh network compatibility can include provisions that enable mesh network compatible modules to keep track of other nearby mesh network compatible modules so that data can be passed through neighboring modules. Mesh network compatibility is essentially the hallmark of the 802.15.4 protocol. In contrast, high power wireless communications circuitry 212 is not a mesh network compatible module and requires an access point in order to communicate to devices in a network. Thus, if a first device having circuitry 212 wants to communicate data to another device having circuitry 212, the first device has to communicate with the access point, which then transmits the data to the second device. There is no device-to-device communication per se using circuitry 212.

Non-volatile memory 216 can be any suitable permanent memory storage such as, for example, NAND Flash, a hard disk drive, NOR, ROM, or phase change memory. In one embodiment, non-volatile memory 216 can store audio clips that can be played back by speaker 218. The audio clips can include installation instructions or warnings in one or more languages. Speaker 218 can be any suitable speaker operable to playback sounds or audio files. Speaker 218 can include an amplifier (not shown).

Sensors 220 can be monitored by system processor 210 and safety processor 230, and can include safety sensors 221 and non-safety sensors 222. One or more of sensors 220 may be exclusively monitored by one of system processor 210 and safety processor 230. As defined herein, monitoring a sensor refers to a processor's ability to acquire data from that monitored sensor. That is, one particular processor may be responsible for acquiring sensor data, and possibly storing it in a sensor log, but once the data is acquired, it can be made available to another processor either in the form of logged data or real-time data. For example, in one embodiment, system processor 210 may monitor one of non-safety sensors 222, but safety processor 230 cannot monitor that same non-safety sensor. In another embodiment, safety processor 230 may monitor each of the safety sensors 221, but may provide the acquired sensor data to system processor 210.

Safety sensors 221 can include sensors necessary for ensuring that hazard detection system 205 can monitor its environment for hazardous conditions and alert users when hazardous conditions are detected, and all other sensors not necessary for detecting a hazardous condition are non-safety sensors 222. In some embodiments, safety sensors 221 include only those sensors necessary for detecting a hazardous condition. For example, if the hazardous condition includes smoke and fire, then the safety sensors might only include a smoke sensor, at least one temperature sensor and a relative humidity sensor. Other sensors, such as non-safety sensors, could be included as part of system 205, but might not be needed to detect smoke or fire. As another example, if the hazardous condition includes carbon monoxide, then the safety sensor might be a carbon monoxide sensor, and no other sensor might be needed to perform this task.

Thus, sensors deemed necessary can vary based on the functionality and features of hazard detection system 205. In one embodiment, hazard detection system 205 can be a combination smoke, fire, and carbon monoxide alarm system. In such an embodiment, detection system 205 can include the following necessary safety sensors 221: a smoke detector, a carbon monoxide (CO) sensor, and one or more temperature sensors. Smoke detectors typically use optical detection, ionization, or air sampling techniques to trigger the smoke condition. Optical scattering and obscuration detection techniques may use infrared light emitting diodes (LEDs) and photodiodes. When smoke and/or other matter (e.g., water vapor) enters a smoke chamber, the light emitted by the LED(s) is scattered, which enables the photodiodes to detect the light. If no smoke or other matter (e.g., water vapor) is in the smoke chamber, then the photodiodes are not able to detect the light being emitted by the LED(s). In some embodiments, multiple LEDs may be incorporated in the smoke sensor. Each LED may emit light energy at different wavelengths. Ionization techniques may use a radioactive material such as Americium-241 to ionize the air, which creates a measurable current between detector two plates. When smoke particles enter the chamber, they bind to the ions. The reaction produces a measurable drop in the conducted current between detector plates; the resulting drop indicates smoke detection. In some geographic locations (e.g., Europe) traditional Americium-241 ionization smoke detectors are banned by regulatory agencies in part because of the necessity to dispose of a radioactive material at the end of the smoke detector's life. A smoke detector can also use a non-radioactive ionization technique to detect the presence of smoke and/or other particulate matter. A non-radioactive ionizing detector may use a LED such as an ultraviolet emitting LED with a photocatalyst coating. The photocatalyst generates ions when light (e.g., UV light) passes through it. When these ions are displaced or neutralized by smoke and/or other matter, the detector detects a change in current between two plates and register a smoke event.

A CO sensor can detect the presence of carbon monoxide gas, which, in the home, is typically generated by open flames, space heaters, water heaters, blocked chimneys, and automobiles. The material used in electrochemical CO sensors typically has a 5-7 year lifespan. Thus, after a 5-7 year period has expired, the CO sensor should be replaced. A heat sensor can be a thermistor, which is a type of resistor whose resistance varies based on temperature. Thermistors can include negative temperature coefficient (NTC) type thermistors or positive temperature coefficient (PTC) type thermistors. A relative humidity sensor may be used to distinguish between obscuration caused by smoke and steam or fog. Furthermore, in this embodiment, detection system 205 can include the following non-safety sensors 222: a humidity sensor, an ambient light sensor, a push-button sensor, a passive infra-red (PIR) sensor, and one or more ultrasonic sensors. A temperature and humidity sensor can provide relatively accurate readings of temperature and relative humidity for the purposes of environmental monitoring and HVAC control. An ambient light sensor (ALS) can detect ambient light and the push-button sensor can be a switch, for example, that detects a user's press of the switch. A PIR sensor can be used for various motion detection features. Ultrasonic sensors can be used to detect the presence of an object. Such sensors can generate high frequency sound waves and determine which wave(s) are received back by the sensor. Sensors 220 can be mounted to a printed circuit board (e.g., the same board that processors 210 and 230 may be mounted to), a flexible printed circuit board, a housing of system 205, or a combination thereof.

In some embodiments, data acquired from one or more non-safety sensors 222 can be acquired by the same processor used to acquire data from one or more safety sensors 221. For example, safety processor 230 may be operative to monitor both safety and non-safety sensors 221 and 222 for power savings reasons, as discussed above. Although safety processor 230 may not need any of the data acquired from non-safety sensor 222 to perform its hazard monitoring and alerting functions, the non-safety sensor data can be utilized to provide enhanced hazard system 205 functionality. The enhanced functionality can be realized in alarming algorithms according to various embodiments discussed herein. For example, the non-sensor data can be utilized by system processor 210 to implement system state machines that may interface with one or more sensor state machines.

Alarm 234 can be any suitable alarm that alerts users in the vicinity of system 205 of the presence of a hazard condition. Alarm 234 can also be activated during testing scenarios. Alarm 234 can be a piezo-electric buzzer, for example.

Power source 240 can supply power to enable operation of system 205 and can include any suitable source of energy. Embodiments discussed herein can include AC line powered, battery powered, a combination of AC line powered with a battery backup, and externally supplied DC power (e.g., USB supplied power). Embodiments that use AC line power, AC line power with battery backup, or externally supplied DC power may be subject to different power conservation constraints than battery only embodiments. Battery powered embodiments are designed to manage power consumption of its finite energy supply such that hazard detection system 205 operates for a minimum period of time. In some embodiments, the minimum period of time can be one (1) year, three (3) years, or seven (7) years. In other embodiments, the minimum period of time can be at least seven (7) years, eight (8) years, nine (9) years, or ten (10) years. Line powered embodiments are not as constrained because their energy supply is virtually unlimited. Line powered with battery backup embodiments may employ power conservation methods to prolong the life of the backup battery.

In battery only embodiments, power source 240 includes one or more batteries or a battery pack. The batteries can be constructed from different compositions (e.g., alkaline or lithium iron disulfide) and different end-user configurations (e.g., permanent, user replaceable, or non-user replaceable) can be used. In one embodiment, six cells of Li—$FeS_2$ can be arranged in two stacks of three. Such an arrangement can yield about 27000 mWh of total available power for system 205.

Power conversion circuitry 242 includes circuitry that converts power from one level to another. Multiple instances of power conversion circuitry 242 may be used to provide the different power levels needed for the components within system 205. One or more instances of power conversion circuitry 242 can be operative to convert a signal supplied by power source 240 to a different signal. Such instances of power conversion circuitry 242 can exist in the foiin of buck converters or boost converters. For example, alarm 234 may require a higher operating voltage than high power wireless communications circuitry 212, which may require a higher operating voltage than processor 210, such that all required voltages are different than the voltage supplied by power source 240. Thus, as can be appreciated in this example, at least three different instances of power conversion circuitry 242 are required.

High quality power circuitry 243 is operative to condition a signal supplied from a particular instance of power conversion circuitry 242 (e.g., a buck converter) to another signal. High quality power circuitry 243 may exist in the form of a low-dropout regulator. The low-dropout regulator may be able to provide a higher quality signal than that provided by power conversion circuitry 242. Thus, certain components may be provided with "higher" quality power than other components. For example, certain safety sensors 221 such as smoke detectors and CO sensors require a more stable voltage in order to operate properly than a digital circuitry within the system processor 210. As will be explained in more detail below, power circuitry may be customized to provide specific power signals for each LED being used in the smoke sensor.

Power gating circuitry 244 can be used to selectively couple and de-couple components from a power bus. De-coupling a component from a power bus insures that the component does not incur any quiescent current loss, and therefore can extend battery life beyond that which it would be if the component were not so de-coupled from the power bus. Power gating circuitry 244 can be a switch such as, for example, a MOSFET transistor. Even though a component is de-coupled from a power bus and does not incur any current loss, power gating circuitry 244 itself may consume a small amount of power. This power consumption, however, is less than the quiescent power loss of the component.

It is understood that although hazard detection system 205 is described as having two separate processors, system processor 210 and safety processor 230, which may provide certain advantages as described hereinabove and hereinbelow, including advantages with regard to power consumption as well as with regard to survivability of core safety monitoring and alarming in the event of advanced feature provision issues, it is not outside the scope of the present teachings for one or more of the various embodiments discussed herein to be executed by one processor or by more than two processors.

Figure 3:
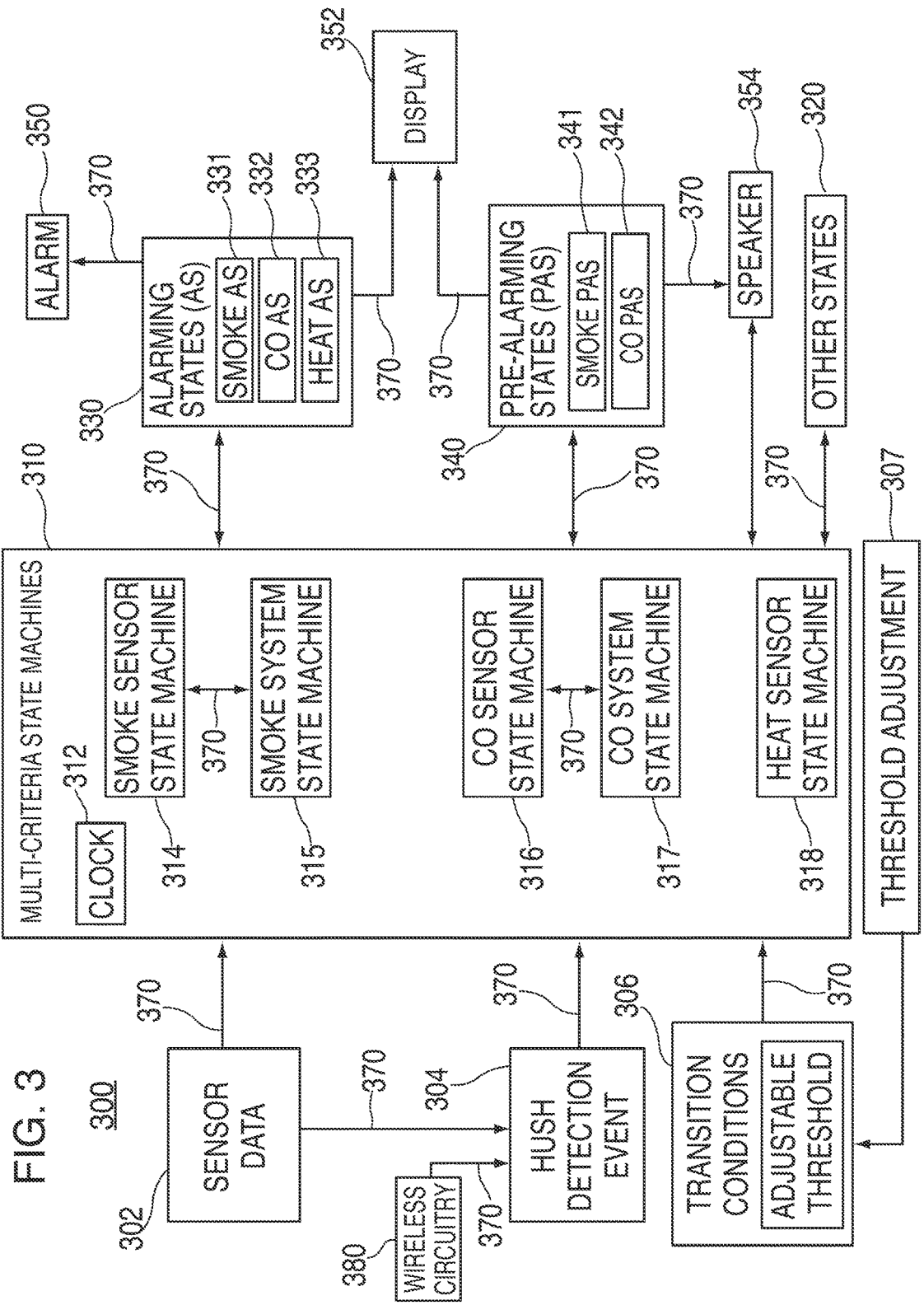
FIG. 3 shows an illustrative block diagram showing various components of a hazard detection system working together to provide multi-criteria alarming and pre-alarming functionality, according to some embodiments.

FIG. 3 shows an illustrative block diagram showing various components of hazard detection system 300 working together to provide multi-criteria alarming and pre-alarming functionalities according to various embodiments. As shown, system 300 can include sensor data 302, hush detection events 304, transition conditions 306, threshold adjustment parameter 307, multi-criteria state machines 310, clock 312, other states 320, alarming states 330, pre-alarming states 340, alarm 350, display 352, speaker 354, wireless circuitry 380. Also shown are several communication links 370, each of which may have unidirectional or bidirectional data and/or signal communications capabilities. Multi-criteria state machines 310 can control alarming states 330, pre-alarming states 340, and all other state machine states 320 based on sensor data 302, hush detection events 304, transition conditions 306, clock 312, and other criteria, and alarming and pre-alarming states 330 and 340 can control the output of alarm 350, display 352, and speaker 354. Alarming states 330 can include multiple alarming states (e.g., one for each hazard, such as smoke alarming state 331, CO alarming state 332, and heat alarming state 333) and pre-alarming states 340 can include multiple pre-alarming states (e.g., one or more for each hazard, such as smoke pre-alarming state 341 and CO pre-alarming state 342. Other states can include, for example, idling states, monitoring states, alarm hushing states, pre-alarm hushing states, post-alarm states, holding states, and alarm monitoring states.

Alarming states 330 can control activation and deactivation of alarm 350 and display 352 in response to determinations made by multi-criteria state machines 310. Alarm 350 can provide audible cues (e.g., in the form of buzzer beeps) that a dangerous condition is present. Display 352 can provide a visual cue (e.g., such as flashing light or change in color) that a dangerous condition is present. If desired, alarming states 330 can control playback of messages over speaker 354 in conjunction with the audible and/or visual cues. For example, combined usage of alarm 350 and speaker 354 can repeat the following sequence: "BEEP, BEEP, BEEP—Smoke Detected In Bedroom—BEEP BEEP BEEP," where the "BEEPS" emanate from alarm 350 and "smoke detected in bedroom" emanates from speaker 354. As another example, usage of alarm 350 and speaker 354 can repeat the following sequence: "BEEP, BEEP, BEEP—Wave to Hush Alarm—BEEP BEEP BEEP," in which speaker 354 is used to provide alarming hush instructions. Any one of the alarming states 330 (e.g., smoke alarm state 331, CO alarm state 332, and heat alarm state 333) can independently control alarm 350 and/or display 352 and/or speaker 354. In some embodiments, alarming states 330 can cause alarm 350 or display 352 or speaker 354 to emit different cues based on which specific alarm state is active. For example, if a smoke alarm state is active, alarm 350 may emit a sound having a first characteristic, but if a CO alarm state is active, alarm 350 may emit a sound having a second characteristic. In other embodiments, alarming states 330 can cause alarm 350 and display 352 and speaker 354 to emit the same cue regardless of which specific alarm state is active.

Pre-alarming states 340 can control activation and deactivation of speaker 354 and display 352 in response to determinations made by multi-criteria state machines 310. Pre-alarming can serve as a warning that a dangerous condition may be imminent. Speaker 354 may be utilized to playback voice warnings that a dangerous condition may be imminent. Different pre-alarm messages may be played back over speaker 354 for each type of detected pre-alarm event. For example, if a smoke pre-alarm state is active, a smoke related message may be played back over speaker 354. If a CO pre-alarm state is active, a CO related message may be played back. Furthermore, different messages may be played back for each one of the multiple pre-alarms associated with each hazard (e.g., smoke and CO). For example, the smoke hazard may have two associated pre-alarms, one associated with a first smoke pre-alarming state (e.g., suggesting that an alarming state may be moderately imminent) and another one associated with a second smoke pre-alarming state (e.g., suggesting that an alarming state may be highly imminent). Pre-alarm messages may also include voice instructions on how to hush pre-alarm messages. Display 352 may also be utilized in a similar fashion to provide visual cues of an imminent alarming state. In some embodiments, the pre-alarm messages can specify the location of the pre-alarming conditions. For example, if hazard system 300 knows it is located in the bedroom, it can incorporate the location in the pre-alarm message: "Smoke Detected In Bedroom."

Hazard detection system 300 can enforce alarm and pre-alarm priorities depending on which conditions are present. For example, if elevated smoke and CO conditions exist at the same time, the smoke alarm state and/or pre-alarm smoke state may take precedence over the CO alarm state and/or CO pre-alarm state. If a user silences the smoke alarm or smoke pre-alarm, and the CO alarm state or CO pre-alarm state is still active, system 300 may provide an indication (e.g., a voice notification) that a CO alarm or pre-alarm has also been silenced. If a smoke condition ends and the CO alarm or pre-alarm is event is still active, the CO alarm or pre-alarm may be presented to the user.

Multi-criteria state machines 310 can transition to an idling state when it determines that relatively little or no dangerous conditions exist. The idling state can enforce a relatively low level of hazard detection system activity. For example, in the idle state, the data sampling rates of one or more sensors may be set at relatively slow intervals. Multi-criteria state machines 310 can transition to a monitoring state when it determines that sensor data values have raised to a level that warrants closer scrutiny, but not to a level that transitions to a pre-alarming or alarming state. The monitoring state can imply a relatively high level of hazard detection system activity. For example, in monitoring state, the data sampling rates of one or more sensors may be much greater than in the idle state. In addition, the data sampling rates of one or more sensors may be set at relatively fast intervals for alarming states 330, pre-alarming states 340, or both.

Alarm hushing and pre-alarm hushing states may refer to a user-instructed deactivation of an alarm or a pre-alarm for a predetermined amount of time. For example, in one embodiment, a user can press a button (not shown) to silence an alarm or pre-alarm. In another embodiment, a user can perform a hush gesture in the presence of the hazard detection system. A hush gesture can be a user initiated action in which he or she performs a gesture (e.g., a wave motion) in the vicinity of system 300 with the intent to turn off or silence a blaring alarm. One or more ultrasonic sensors, a PIR sensor, or a combination thereof can be used to detect this gesture. In another approach, wireless circuitry 370 may receive instructions to hush the alarm. For example, a user may use his or her phone to transmit a hush command via a wireless protocol (e.g., Bluetooth low energy) to system 300, whereupon wireless circuitry 380 may forward that command to trigger a hush detection event 304.

Post-alarming states may refer to states that multi-criteria state machines 310 can transition to after having been in one of alarming states 330 or one of pre-alarming states 340. In one post-alarming state, hazard detection system 300 can provide an "all clear" message to indicate that the alarm or pre-alarm condition is no longer present. This can be especially useful, for example, for CO because humans cannot detect CO. Another post-alarming state can be a holding state, which can serve as a system debounce state. This state can prevent hazard detection system 300 from immediately transitioning back to a pre-alarming state 340 after having just transitioned from an alarming state 330.

Multi-criteria state machines 310 can include several different state machines: sensor state machines and system state machines. Each state machine can be associated with a particular hazard such as, for example, a smoke hazard, a carbon monoxide hazard, or a heat hazard, and the multi-criteria state machines may leverage data acquired by one or more sensors in managing detection of a hazard. In some embodiments, a sensor state machine can be implemented for each hazard. In other embodiments, a system state machine may be implemented for each hazard or a subset of hazards. The sensor state machines can be responsible for controlling relatively basic hazard detection system functions and the system state machines can be responsible for controlling relatively advanced hazard detection system functions. In managing detection of a hazard, each sensor state machine and each system state machine can transition among any one of its states based on sensor data 302, hush events 304, and transition conditions 306. A hush event can be a user initiated command to hush, for example, a sounding alarm or pre-alarm voice instruction.

Transition conditions 306 can include a myriad of different conditions that may define how a state machine transitions from one state to another. Each state machine can have its own set of transition conditions. The conditions can define thresholds that may be compared against any one or more of the following inputs: sensor data values, time clocks, and user interaction events (e.g., hush events). State change transitions can be governed by relatively simple conditions (e.g., single-criteria conditions), or relatively complex conditions (e.g., multi-criteria conditions). Single-criteria conditions may compare one input to one threshold. For example, a simple condition can be a comparison between a sensor data value and a threshold. If the sensor data value equals or exceeds the threshold, the state change transition may be executed. In contrast, a multi-criteria condition can be a comparison of one or more inputs to one or more thresholds. For example, a multi-criteria condition can be a comparison between a first sensor value and a first threshold and a comparison between a second sensor value and a second threshold. In some embodiments, both comparisons would need to be satisfied in order to effect a state change transition. In other embodiments, only one of the comparisons would need to be satisfied in order to effect a state change transition. As another example, a multi-criteria condition can be a comparison between a time clock and a time threshold and a comparison between a sensor value and a threshold.

In some embodiments, the threshold for a particular transition condition can be adjusted. Such thresholds are referred to herein as adjustable thresholds (e.g., shown as part of transition conditions 306). The adjustable threshold can be changed in response to threshold adjustment parameter 307, which may be provided, for example, by an alarm threshold setting module according to an embodiment. Adjustable thresholds can be selected from one of at least two different selectable thresholds, and any suitable selection criteria can be used to select the appropriate threshold for the adjustable threshold. In one embodiment, the selection criteria can include several single-criteria conditions or a multi-criteria condition. In another embodiment, if the adjustable threshold is compared to sensor values of a first sensor, the selection criteria can include an analysis of at least one sensor other than the first sensor. In another embodiment, the adjustable threshold can be the threshold used in a smoke alarm transition condition, and the adjustable threshold can be selected from one of three different thresholds.

In some embodiments, the threshold for a particular transition condition can be a learned condition threshold (not shown). The learned condition threshold can be the result of a difference function, which may subtract a constant from an initial threshold. The constant can be changed, if desired, based on any suitable number of criteria, including, for example, heuristics, field report data, software updates, user preferences, device settings, etc. Changing the constant can provide a mechanism for changing the transition condition for one or more states (e.g., a pre-alarming state). This constant can be provided to transition conditions 306 to make adjustments to the learned condition threshold. In one embodiment, the constant can be selected based on installation and setup of hazard detection system 300. For example, the home owner can indicate that hazard detection system 300 has been installed in a particular room of an enclosure. Depending on which room it is, system 300 can select an appropriate constant. For example, a first constant can be selected if the room is a bedroom and a second constant can be selected if the room is a kitchen. The first constant may be a value that makes hazard detection system 300 more sensitive to potential hazards than the second constant because the bedroom is in a location that is generally further away from an exit and/or is not generally susceptible to factors that may otherwise cause a false alarm. In contrast, the kitchen, for example, is generally closer to an exit than a bedroom and can generate conditions (e.g., steam or smoke from cooking) that may cause a false alarm. Other installation factors can also be taken into account in selecting the appropriate constant. For example, the home owner can specify that the room is adjacent to a bathroom. Since humidity stemming from a bathroom can cause false alarms, hazard system 300 can select a constant that takes this into account. As another example, the home owner can specify that the room includes a fireplace. Similarly, hazard system 300 can select a constant that takes this factor into account.

In another embodiment, hazard detection system 300 can apply heuristics to self-adjust the constant. For example, conditions may persist that keep triggering pre-alarms, but the conditions do not rise to alarming levels. In response to such persistent pre-alarm triggering, hazard detection system 300 can modify the constant so that the pre-alarms are not so easily triggered. In yet another embodiment, the constant can be changed in response to a software update. For example, a remote server may analyze data acquired from several other hazard detection systems and adjust the constant accordingly, and push the new constant to hazard detection system 300 via a software update. In addition, the remote server can also push down constants based on user settings or user preferences to hazard detection system 300. For example, the home owner may be able to define a limited number of settings by directly interacting with hazard detection system 300. However, the home owner may be able to define an unlimited number of settings by interacting with, for example, a web-based program hosted by the remote server. Based on the settings, the remote server can push down one or more appropriate constants.

The sensor state machines can control alarming states 330 and one or more of other states 320. In particular, smoke sensor state machine 314 can control smoke alarm state 331, CO sensor state machine 316 can control CO alarming state 332, and heat sensor state machine 318 can control heat alarming state 333. For example, smoke sensor state machine 314 may be operative to sound alarm 350 in response to a detected smoke event. As another example, CO sensor state machine 316 can sound alarm 350 in response to a detected CO event. As yet another example, heat sensor state machine 318 can sound alarm 350 in response to a detected heat event. In some embodiments, a sensor state machine can exercise exclusive control over one or more alarming states 330.

The system state machines can control pre-alarming states 340 and one or more of other states 320. In particular, smoke system state machine 315 may control smoke pre-alarm state 341, and CO system state machine 317 may control CO pre-alarm state 342. In some embodiments, each system state machine can manage multiple pre-alarm states. For example, a first pre-alarm state may warn a user that an abnormal condition exists, and a second pre-alarm state may warn the user that the abnormal condition continues to exist. Moreover, each system state machine can manage other states that cannot be managed by the sensor state machines. For example, these other states can include a monitoring state, a pre-alarm hushing state, and post-alarm states such as holding and alarm monitoring states.

The system state machines can co-manage one or more states with sensor state machines. These co-managed states ("shared states") can exist as states in both system and sensor state machines for a particular hazard. For example, smoke system state machine 315 may share one or more states with smoke sensor state machine 314, and CO system state machine 317 may share one or more states with CO sensor state machine 316. The joint collaboration between system and sensor state machines for a particular hazard is shown by communications link 370, which connects the two state machines. In some embodiments, any state change transition to a shared state may be controlled by the sensor state machine. For example, the alarming state may be a shared state, and anytime a sensor state machine transitions to the alarming state, the system state machine that co-manages states with that sensor state machine may also transition to the alarming state. In some embodiments, shared states can include idling states, alarming states, and alarm hushing states. The parameters by which multi-criteria state machines 310 may function are discussed in more detail in connection with the description accompanying FIGS. 4A-8B of U.S. Provisional Patent Application No. 61/847,937.

Figure 4:
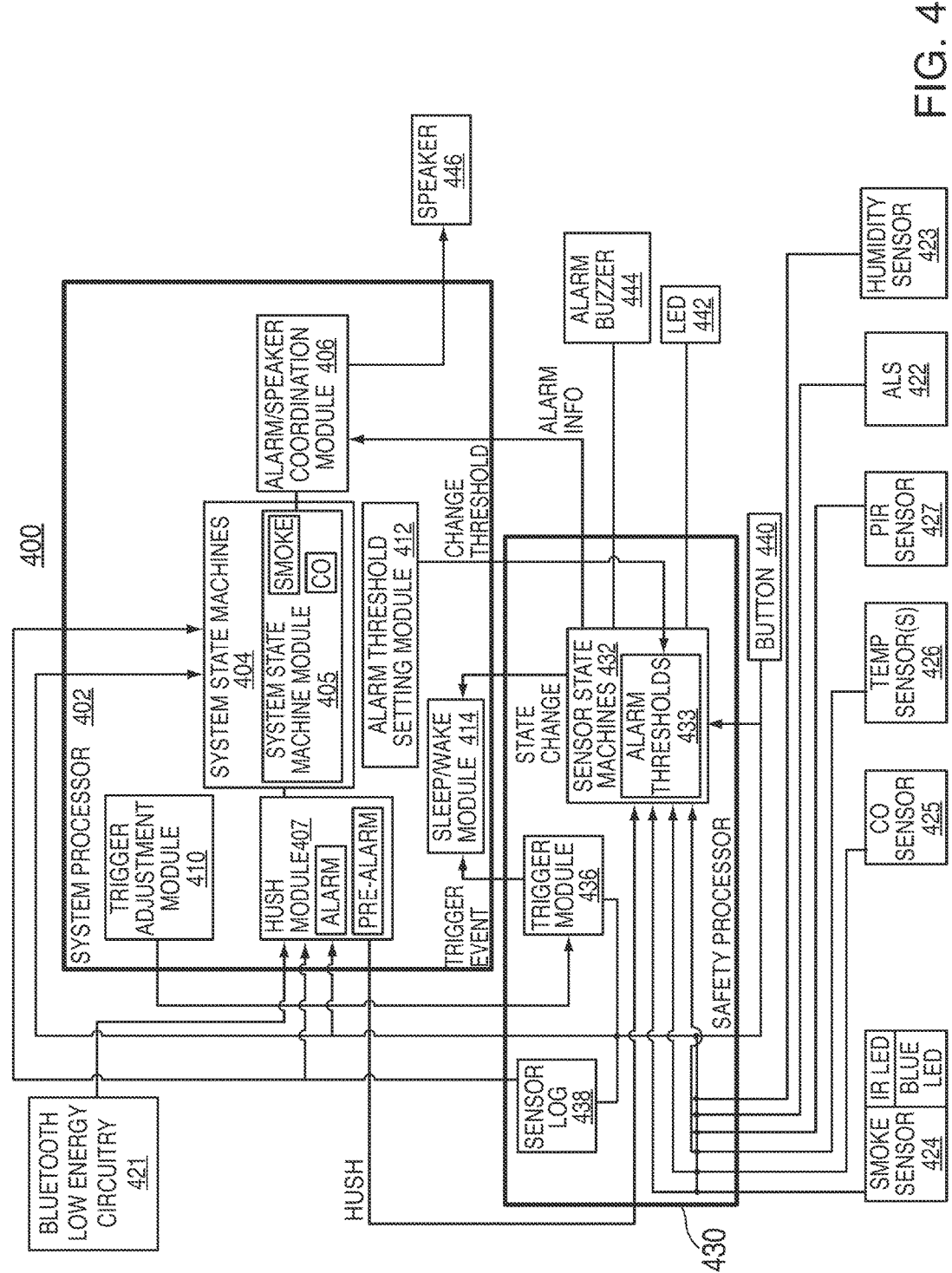
FIG. 4 shows an illustrative schematic of a hazard detection system, according to some embodiments.

FIG. 4 shows an illustrative schematic of hazard detection system 400 according to an embodiment and shows, among other things, signal paths among various components, state machines, and illustrative modules being executed by different processors. System 400 can include system processor 402, safety processor 430, Bluetooth low energy circuitry 421, ALS sensor 422, humidity sensor 423, smoke sensor 424 (which may include an Infrared LED and a blue LED), CO sensor 425, temperatures sensors 426, and PIR sensor 427, button 440, LED(s) 442, alarm 444, speaker 446, fabric network communications module 450, and fabric network communications circuitry 460. System processor 402 can be similar to system processor 210 of FIG. 2. System processor 402 can operate system state machines 404, system state machine module 405, alarm/speaker coordination module 406, hush module 407, trigger adjustment module 410, and sleep/wake module 414. System state machines 404 can access system state machine module 405, alarm/speaker coordination module 406, and hush module 407 in making state change determinations. System processor 402 can receive data values acquired by Bluetooth circuitry 421 and other inputs from safety processor 430. System processor 402 may receive data from sensors 422-427, data from sensor log 438, trigger events from trigger module 436, state change events and alarm information from sensor state machines 432, and button press events from button 440.

Safety processor 430 can be similar to safety processor 230 of FIG. 2. Safety processor 430 can operate sensor state machines 432, alarm thresholds 433, trigger module 436, and sensor log 438. Safety processor 430 can control operation of LEDs 442 and alarm 444. Safety processor 430 can receive data values acquired by sensors 422-427 and button 440. All or a portion of acquired sensor data can be provided to sensor state machines 432. For example, as illustrated in FIG. 4, smoke, CO, and heat sensor data is shown being directly provided to sensor state machines 432. Sensor log 438 can store chunks of acquired data that can be provided to system processor 402 on a periodic basis or in response to an event such as a state change in one of sensor state machines 432 or a trigger event detected by trigger module 436. In addition, in some embodiments, even though the sensor data may be stored in sensor log 438, it can also be provided directly to system processor 402, as shown in FIG. 4.

Alarm thresholds 433 can store the alarming thresholds in a memory (e.g., Flash memory) that is accessible by sensor state machines 432. As discussed above, sensor state machines 432 can compare monitored sensor data values against alarm thresholds 433 that may be stored within safety processor 430 to determine whether a hazard event exists, and upon determining that the hazard event exists, may cause the alarm to sound. Each sensor (e.g., smoke sensor, CO sensor, and heat sensor) may have one or more alarm thresholds. When multiple alarm thresholds are available for a sensor, safety processor 430 may initially select a default alarm threshold, but responsive to an instruction received from system processor 402 (e.g., from Alarm/Pre-Alarm Threshold Setting Module 412), it can select one of the multiple alarm thresholds as the alarm threshold for that sensor. Safety processor 430 may automatically revert back to the default alarm threshold if certain conditions are not met (e.g., a predetermined period of time elapses in which an alarm setting threshold instruction is not received from system processor 402).

Safety processor 430 and/or system processor 402 can monitor button 440 for button press events. Button 440 can be an externally accessible button that can be depressed by a user. For example, a user may press button 440 to test the alarming function or to hush an alarm. Safety processor 430 can control the operation of alarm 444 and LEDs 442. Processor 430 can provide alarm information to alarm/speaker coordination module 406 so that module 406 can coordinate speaker voice notification with alarm sounds. In some embodiments, safety processor 430 is the only processor that controls alarm 444. Safety processor 430 can also receive inputs from system processor 402 such as hush events from hush module 407, trigger band boundary adjustment instructions from trigger adjustment module 410, and change threshold instructions from alarm/pre-alarm threshold setting module 412.

As shown, hazard detection system 400 may use a bifurcated processor arrangement to execute the multi-criteria state machines to control the alarming and pre-alarming states, according to various embodiments. The system state machines can be executed by system processor 402 and the sensor state machines can be executed by safety processor 430. As shown, sensor state machines 432 may reside within safety processor 430. This shows that safety processor 430 can operate sensor state machines such as a smoke sensor state machine, CO sensor state machine, and heat sensor state machine. Thus, the functionality of the sensor state machines (as discussed above) are embodied and executed by safety processor 430. As also shown, system state machines 404 may reside within system processor 402. This shows that system processor 402 can operate system state machines such as a smoke system state machine and a CO system state machine. Thus, the functionality of the system state machines (as discussed above) are embodied and executed by system processor 402.

In the bifurcated approach, safety processor 430 can serve as the "brain stem" of hazard detection system 400 and system processor 402 can serve as the "frontal cortex." In human terms, even when a person goes to sleep (i.e., the frontal cortex is sleeping) the brain stem maintains basic life functions such as breathing and heart beating. Comparatively speaking, safety processor 430 is always awake and operating; it is constantly monitoring one or more of sensors 422-427, even if system processor 402 is asleep or non-functioning, and manauinu the sensor state machines of hazard detection system 400. When the person is awake, the frontal cortex is used to processes higher order functions such as thinking and speaking Comparatively speaking, system processor 402 performs higher order functions implemented by system state machines 404, alarm/speaker coordination module 406, hush module 407, trigger adjustment module 410, and alarm/pre-alarm threshold setting module 412. In some embodiments, safety processor 430 can operate autonomously and independently of system processor 402. Thus, in the event system processor 402 is not functioning (e.g., due to low power or other cause), safety processor 430 can still perform its hazard detection and alarming functionality.

The bifurcated processor arrangement may further enable hazard detection system 400 to minimize power consumption by enabling the relatively high power consuming system processor 402 to transition between sleep and non-sleep states while the relatively low power consuming safety processor 430 is maintained in a non-sleep state. To save power, system processor 402 can be kept in the sleep state until one of any number of suitable events occurs that wakes up system processor 402. Sleep/wake module 414 can control the sleep and non-sleep states of system processor 402. Safety processor 430 can instruct sleep/wake module 414 to wake system processor 402 in response to a trigger event (e.g., as detected by trigger module 436) or a state change in sensor state machines 432. Trigger events can occur when a data value associated with a sensor moves out of a trigger band associated with that sensor. A trigger band can define upper and lower boundaries of data values for each sensor and are stored with safety processor 430 in trigger module 436. Trigger module 436 can monitor sensor data values and compare them against the boundaries set for that particular sensor's trigger band. Thus, when a sensor data value moves out of band, trigger module 436 registers this as a trigger event and notifies system processor 402 of the trigger event (e.g., by sending a signal to sleep/wake module 414).

The boundaries of the trigger band can be adjusted by system processor 402, when it is awake, based on an operational state of hazard detection system 400. The operational state can include the states of each of the system and sensor state machines, sensor data values, and other factors. System processor 402 may adjust the boundaries of one or more trigger bands to align with one or more system state machine states before transitioning back to sleep. Thus, by adjusting the boundaries of one or more trigger bands, system processor 402 effectively communicates "wake me" instructions to safety processor 430. The "wake me" instructions can be generated by trigger adjustment module 410 and transmitted to trigger module 436, as shown in FIG. 4. The "wake me" instructions can cause module 436 to adjust a boundary of one or more trigger bands.

Figure 5:
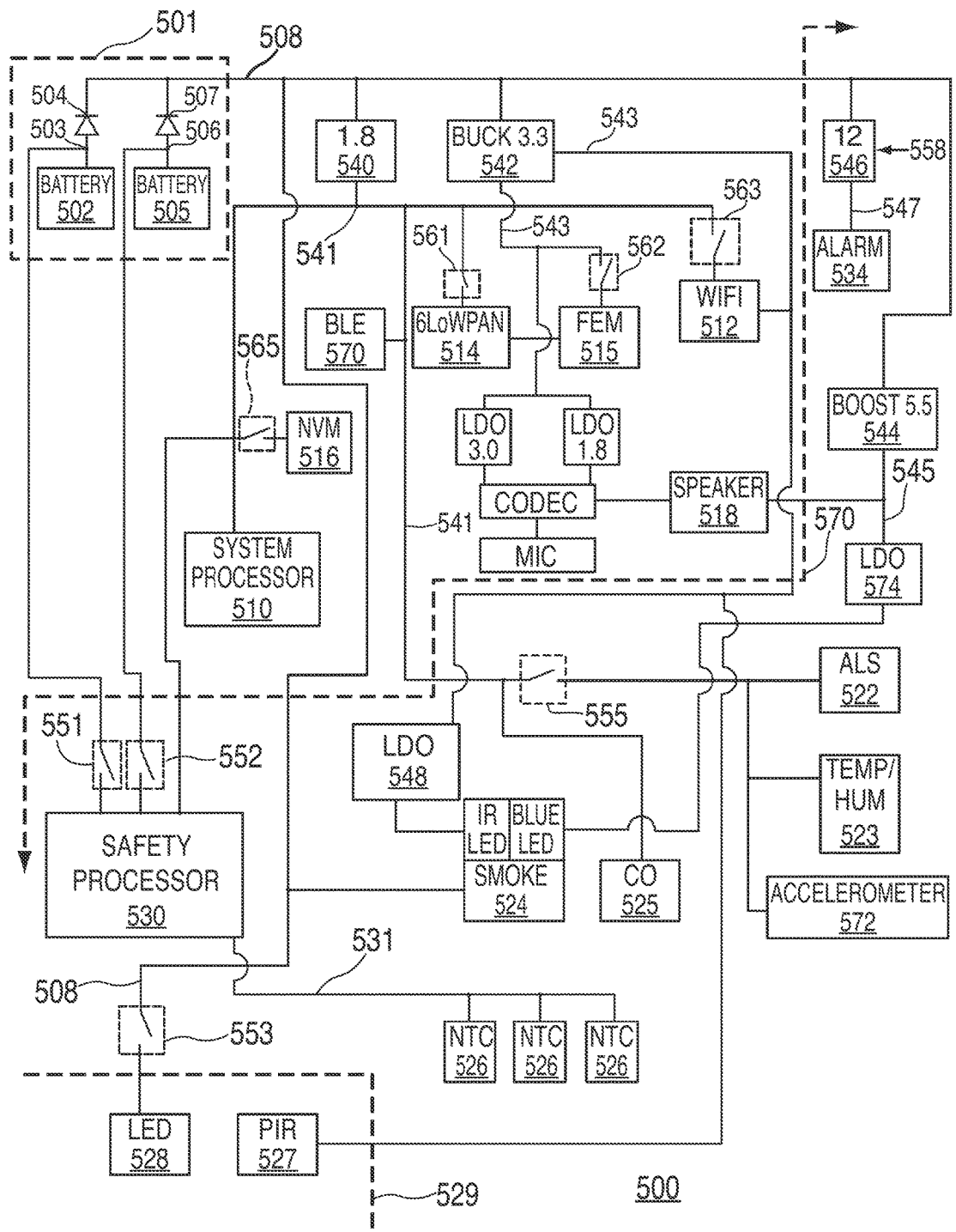
FIG. 5 shows an illustrative circuit schematic of hazard detection system according to an embodiment.

FIG. 5 shows an illustrative circuit schematic of hazard detection system 500 according to an embodiment. The circuit schematic is a more detailed illustrative representation of hazard detection system 205 (of FIG. 2) and shows, among other things, power consuming components, the power busses supplying power to the components, and gating circuitry for selecting coupling and de-coupling components to a power bus.

Hazard detection system 500 can includes battery system 501 operative to provide a DC power source to power bus 508. The DC power source can exist on power bus 508 at a first voltage level. The voltage level may change slightly depending on various conditions, such as changes in temperature. Depending on composition of DC power source (e.g., alkaline or Lithium-based chemistries), the voltage level can vary, for example, between 3.6-5.4 volts. The voltage level may drop substantially when the energy stored in battery system 501 falls below a predetermined threshold (e.g., when the batteries are effectively dead). Battery system 501 can include battery cell group 502 and battery cell group 505. Each of battery cell groups 502 and 505 can include one or more battery cells. In one embodiment, each cell group includes three battery cells. As shown, battery cell group 502 is coupled to diode 504 and to safety processor 530 via bus 503 and gating circuitry 551. Safety processor 530 is similar in many respects to safety processor 230 (discussed above in connection with FIG. 2). Battery cell group 505 is coupled to diode 507 and to safety processor 530 via bus 506 and gating circuitry 552. Safety processor 530 can temporarily close gating circuitries 551 and 552 to measure the voltages of battery groups 502 and 505, respectively. After the measurement is complete, safety processor 530 can open gating circuitry 551 and 552. Diodes 504 and 507 are coupled to power bus 508.

Power bus 508 can be coupled to receive power from a line power source (not shown) that converts AC power to DC power. For example, the line power can be regulated to provide 5.0 volts. In addition, power bus 508 can be coupled to receive power from another DC source such as a USB port (not shown). For example, the other DC source can provide voltage between 4.4-5.25 volts. As a result, the voltage provided on power bus 508 can range from a first voltage (e.g., 3.6 volts) to a second voltage (e.g., 5.25 volts).

Power bus 508 can be coupled to power converter circuitry 540, power converter circuitry 542, power converter circuitry 544, power converter circuitry 546, smoke detector 524, and display module 528 (e.g., light emitting diode (LED)) via power gating circuitry 553. As discussed above in connection with FIG. 2, power converting circuitry is operative to convert a signal from one level to another. Smoke detector 524 can be one of the safety sensors (as previously discussed). Display module 528 can be any suitable display apparatus. In one embodiment, display module 528 can include one or more LEDs that emit different colored light to signify a status of system 500. For example, display of green light can signify good status, orange light can signify a warning condition such as a low battery, and red light can signify a hazard condition. Each of the components on power bus 508 is coupled to receive DC power at the first voltage level. Although smoke detector 524 display module 528 can operate using DC power at the first voltage level, other components in system 500 can require different operating voltages. In addition, it is understood that although various components such as smoke detector 524 and display module 528 can receive power from power bus 508 at a first voltage level, one or more of these components may have internal power conversion circuitry. For example, display module 528 can include a boost converter.

Power converter circuitry 540, 542, 544, and 546 are each operative to convert the DC power signal provided on power bus 508 to a signal having a different voltage level. Power converter circuitry 540 and 542 can all be operative to down convert the DC power signal to three different voltages levels lower than the first voltage level. More particularly, power converter circuitry 540 can be a buck converter that provides a signal having a second voltage level (e.g., 1.8 volts) to power bus 541. Power bus 541 can be coupled to system processor 510 (e.g., which can be similar to processor 210 of FIG. 2), safety processor 530, 6LoWPAN module 514 (e.g., which can be similar to low power wireless communication circuitry 214 of FIG. 2) via power gating circuitry 561, WiFi module 512 (e.g., which can be similar to high power wireless communication circuitry 212 of FIG. 2) via power gating circuitry 563, CO sensor 525, non-volatile memory 516 (e.g., which can be similar to non-volatile memory 216) via power gating circuitry 565, and ambient light sensor 522, temperature and humidity sensor 523, and accelerometer 572 via power gating circuitry 555, and Bluetooth low energy circuitry 570.

Power converter circuitry 562 can be a buck converter that provides a signal having a third voltage level (e.g., 3.3 volts) to power bus 543. Power bus 343 can be coupled to RF Front-End Module (FEM) 515 via power gating circuitry 562, PIR sensor 527, and low-drop out regulator (LDO) 548. LDO 548 may be coupled to the IR LED of smoke sensor 524. RF FEM 515 operates in connection with 6LoWPAN module 514 and can include a power amplifier (PA) for transmitting data, a low-noise amplifier (LNA) for receiving data, an optional antenna switch, and an optional transmit/receive switch. The PA boosts the power of the transmitting signal to improve signal range and the LNA improves sensitivity when receiving a signal. 6LoWPAN module 514 can optionally leverage FEM 515 to improve its performance, but doing so incurs a power penalty. ALS sensor 522 and temperature and humidity sensor 523 can be similar to safety sensors 232 discussed above in connection with FIG. 2. For some embodiments, the module 514 can be a Thread module, corresponding to one particularly useful protocol known as Thread, which is promulgated by the Thread Group and based on 802.15.4, IETF IPv6, and 6LoWPAN.

Power converter circuitry 344 can be a boost converter that provides a signal having a fourth voltage level (e.g., 5.5 volts) to power bus 545. Power converting circuitry 344 can be operative to be selectively turned ON and OFF. Power bus 545 can be coupled to speaker 518 and LDO 574. Speaker 518 can be similar to speaker 218 (discussed above in connection with FIG. 2). The fourth voltage level can be higher than the third voltage level and any voltage provided on power bus 508. LDO 574 may be coupled to the Blue LED of smoke sensor 524.

Power converting circuitry 546 can be operative to up convert the DC power signal to a voltage level higher than the first voltage level. Power converting circuitry 546 can be operative to be selectively turned ON and OFF, depending on a signal applied to node 558. Power converting circuitry 546 can be a boost converter that provides a signal having a fifth voltage (e.g., 12 volts) to power bus 547. Alarm 534 can be similar to alarm 534 (discussed above in connection with FIG. 2).

It is understood that although power converting circuitry 540, 542, 544, 546 were described above as having either a buck converting topology or boost converting topology, any suitable converting topologies can be used. For example, other DC-DC converting topologies such as buck-boost can be used. In addition, converting topologies that use transformers can be used, such as, for example, full-bridge forward converters, half bridge forward converters, single-ended converters, push pull converters, and clamp converters.

Some of the sensors may include subcomponents that have separate power requirements, and as such, may need to be separately powered. Such sensors may be coupled to receive power from two or more power busses so that the subcomponents are supplied with the appropriate power. In some embodiments, one or more of the subcomponents of a sensor may be power gated ON and OFF. For example, smoke detector 524 can be an active sensor that "interrogates" air contained within a chamber with an IR LED and a blue LED, and then monitors for scatted IR and blue light. Thus, in some embodiments, smoke detector 524 can include a smoke detection optical source (a first subcomponent) and a first optical sensor (e.g., IR LED) and second optical sensor (e.g., Blue LED), with each of these components being separately powered. In particular, power bus 508 can provide power to the smoke detection sensor, power bus 543 can provide power to the IR LED, and power bus 545 can provide power to the blue LED.

Low-dropout regulators 548 and 574 may function as substantially constant current sources to drive their respective LEDs. Thus, smoke sensor 524 is being provided with power from different power busses. As will be explained in more detail below, by separately driving each LED in smoke sensor 524, enhanced efficiencies can be realized that are not possible using only one power bus.

System 500 can include one or more thermistors 526 situated in various locations within system 500. Thermistors 526 can be another one of the safety sensors as previously discussed in connection with FIG. 2. As shown, thermistors 526 are NTC type thermistors, though it is understood that other types of thermistors can be used. Thermistors 526 can be coupled to safety processor 530 via power bus 531. Safety processor 530 can selectively provide a power signal to power bus 531. For example, when safety processor 530 desires to take temperature readings from thermistor 526, it can provide power to power bus 531. After the reading is taken, processor 530 can shut off the power to power bus 531. In another embodiment, processor 530 can constantly supply power to power bus 531. It will be understood that any number of thermistors may be used in system 500 and that the thermistors may reside in different locations thereof. For example, in one embodiment, a single thermistor may reside on circuit board 529.

The various components and power busses of hazard detection system 500 can reside on one or more printed circuit boards or flexible printed circuit boards. In one embodiment, PIR sensor 527 and display module 528 can reside on printed circuit board 529 and all other components can reside on another printed circuit board (not shown). In another embodiment, all components can reside on a printed circuit board.

FIG. 5 shows a dashed line 570 snaking between various components of system 500. Dashed line 570 demarcates an illustrative divide of components dedicated to providing 1) safety features and 2) enhanced features, and in particular, generally shows how power is managed by processors 510 and 530. Components generally associated with safety features are shown below dashed line 570 and components generally associated with enhanced features are shown above dashed line 570. Dashed line 570 further serves to illustrate the bifurcated processors embodiment in which safety processor 530 is dedicated to safety features and system processor 510 is dedicated to handling enhanced features as well as general system administration. As will be discussed in more detail below, dashed line shows that safety processor 530 manages power consumption of the "safety" components and system processor manages power consumption of the other components.

The safety features of system 500 are robust, power efficient, and operate without fail. To ensure the robust and power efficient use of the safety features, system 500 can operate as follows. Power converting circuitry 540 and 542 can be operative to always be ON (at least during intended and ordinary usage of system 500) throughout its minimum operational lifespan. There may be instances in which power converting circuitry 540 and 542 are not always ON, such as when the system 500 undergoes a fill power-cycle reset. This way, power supplied on power busses 541 and 543 is always available to downstream components. These components can include system processor 510, safety processor 530, non-volatile memory 516, low-dropout regulator 348, low dropout regulator 574, and the safety sensors (e.g., ALS sensor 522, temperature and humidity sensor 523, smoke detector 524, CO sensor 525, thermistors 526, and PIR sensor 527). That safety processor 530 and the safety sensors have access to power via always ON power converting circuitry 540 and 542 ensures that system 500 is constantly monitoring for hazard events.

Power savings can be realized because safety processor 530, as opposed to system processor 510, is dedicated to monitoring the safety sensors for a hazard condition. Additional power savings can be realized by power gating various components. In particular, safety processor 530 can independently control each of power gating circuits 553 and 555. Thus, processor 530 can selectively couple and de-couple display module 528 to power bus 508, and each of ALS sensor 522, temperature and humidity sensor 523, and accelerometer 572 to power bus 541 by controlling power gating circuits 553 and 355, respectively.

Safety processor 530 can further manage power consumption by selectively enabling power converting circuitry 546. Processor 530 can enable or disable circuitry 546 by applying the appropriate signal to control node 558. When converting circuitry 546 is enabled, it can provide a signal at the fifth voltage level to power bus 547. Processor 530 can enable circuitry 546 when a hazard event is detected, and once circuitry 546 is enabled, alarm 534 is operative to sounds its alarm. When no hazard event is detected or there is no need for alarm 534 to be active, processor 530 can disable circuitry 546. Disabling circuitry 546 saves power lost during the operation of circuitry 546 and as well as power that would otherwise be consumed by alarm 534.

Power management can also be exercised by processor 510. Processor 510 can independently control each of power gating circuits 561, 562, 563, 565, and others (not shown). Thus, processor 510 can selectively couple and de-couple 6loWPAN module 514 to power bus 541, FEM 515 to power bus 543, WiFi module 512 to power bus 541, non-volatile memory 516 to power bus 541, controlling the appropriate power gating circuits. These power-gating compatible components can be completely disconnected from a power bus and still be able to function properly when re-connected to their respective power busses.

System processor 510 can further manage power consumption by selectively enabling power converting circuitry 544. Processor 510 can enable or disable circuitry 544 by applying the appropriate signal to control node 568. When converting circuitry 544 is enabled, it can provide a signal at the fourth voltage level to power bus 545. Processor 510 can enable circuitry 544 when WiFi module 512 and speaker 518 require power. Disabling circuitry 544 saves power lost during the operation of circuitry 544 and as well as power that would otherwise be consumed by WiFi module 512 and speaker 518.

System processor 510 and safety processor 530 can operate according to several different power modes. For example, in a very simplistic sense, both processors 510 and 530 can operate in an active mode and a sleep mode. As another example, one or more of processor 510 and 530 can have multiple active modes and multiple sleep modes, each having a different power consumption level. The particular mode each processor operates in may depend on the mode operation of the system 500. For example, if system 500 is in an Idle mode of operation, system processor 510 may be a relatively deep sleep mode, and safety processor 530 may be in a relatively low power active mode.

Figure 6:
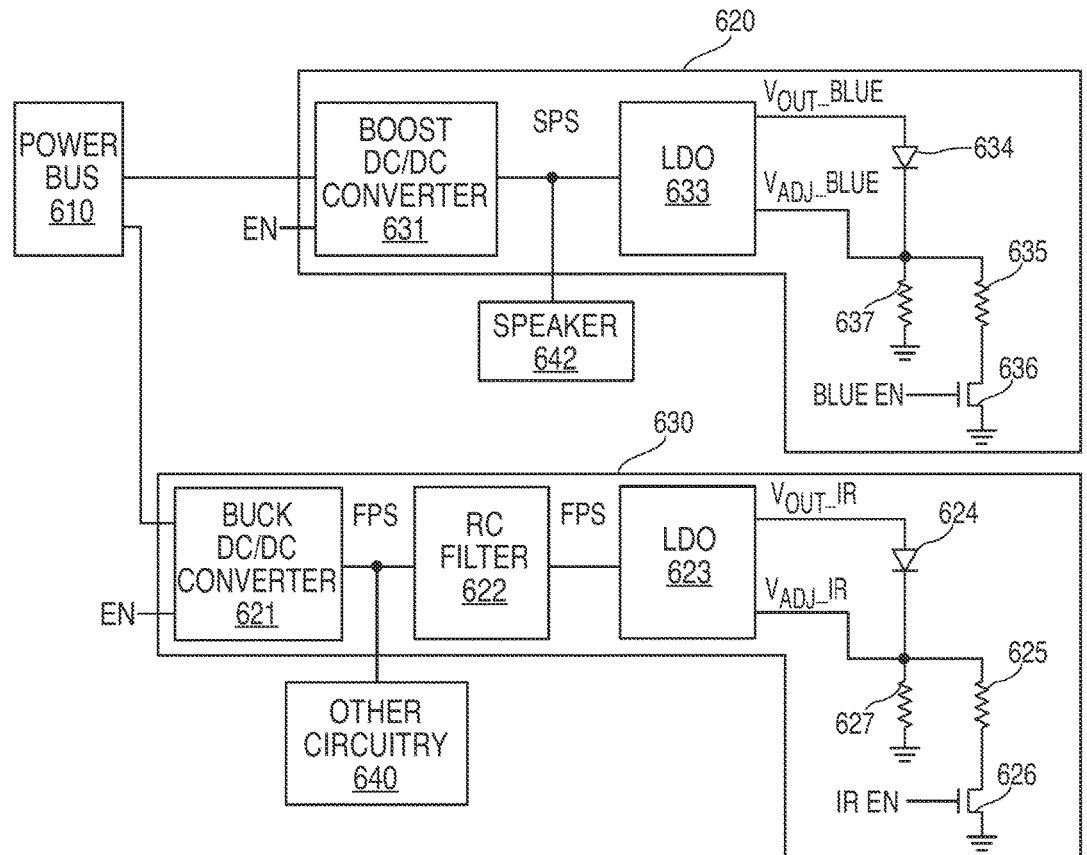
FIG. 6 shows an illustrative schematic of a dual LED driving circuitry according to an embodiment.

FIG. 6 shows an illustrative schematic of a dual LED driving circuitry 600 according to an embodiment. As shown, circuitry 600 includes power source 610, first LED driving circuitry 620, and second LED driving circuitry 630. Power bus 610 may receive power from any one a several different power sources that provide power to the hazard system (not shown). As discussed above, the power source can be a battery or several batteries, AC line power that is converted to DC power for the system, USB power, or any other suitable power source. The voltage provided by the power source can vary from a first voltage to a second voltage. Both LED driving circuitry 620 and 630 receive power from power bus 610. In one embodiment, LED driving circuitry 620 may drive an infrared LED and LED driving circuitry 630 may drive a blue LED.

LED driving circuitry 620 can include buck dc/dc converter 621, RC filter 622, low dropout regulator (LDO) 623, light emitting diode (LED) 624, current setting resistor 625, switch 626, and optional resistor 627, all connected as shown. When converter 621 is enabled, it can provide a first power signal (shown as FPS) characterized as having a voltage level less than the first and second potential voltage values provided at power bus 610. The first power signal can be provided to RC filter 622 and other circuitry 640. Other circuitry 640 can represent all other circuitry within the hazard system that receives power from buck converter 621. In some embodiments, when other circuitry 640 and LED 624 are simultaneously operating, an above limit current may be pulled from the power source. RC filter 622 may prevent the above limit current situation from occurring. RC filter 622 may be specifically tuned based on a known duration of a current pulse being applied to LED 624. Thus, the resistor and capacitor of RC filter are sized appropriately to limit current drawn from converter 621. The current pulse can be controlled by a processor that selectively applies a signal to the IR_EN pin of switch 626.

LDO 623 can receive the first power signal and operate as a substantially constant current source for first LED 624. LDOs are typically used to provide a constant voltage, but LDO 623 has been repurposed to provide a constant current. Current setting resistor 625 can set the current drawn by LED 624 when switch 626 is turned ON (verify this statement; or are resistors 625 and 627 used to set the LED current). LDO 623 can have an internal error amplifier that will drive the output voltage (shown as Vout_IR) to ensure that the feedback voltage (shown as Vadj_IR) is set to a reference voltage. LDO 623 can function properly so long as the first power signal exceeds the sum of the forward drop voltage and the feedback voltage of LED 624. During operation, a processor may turn on switch 626 by applying an appropriate signal thereto, wait a fixed period of time, and then turn switch 626 off. When LDO 623 is turned on, it may transition through a soft-start phase and then regulate the current as desired, and then ramp down when turned off. This produces a consistent and tightly controlled light pulse across the range of input voltages. An advantage of using LDO 623 as the current source is that (switching converter) ripple is removed from the signal, thereby eliminating the potential for creating noise.

LED driving circuitry 630 can include boost dc/dc converter 631, low dropout regulator (LDO) 633, light emitting diode (LED) 634, current setting resistor 635, switch 636, and optional resistor 637, all connected as shown. When converter 631 is enabled, it can provide a second power signal (shown as SPS) characterized as having a voltage level greater than the first and second potential voltage values provided at power bus 610. Boost converter 631 may be coupled to provide the second power signal to other circuitry such as speaker 642. Boost converter 631 may be enabled by a processor to supply power to LED 634, speaker 642, or both.

The operation of LDO 633 and LED 634 may operate in a manner similar as to how LDO 623 and LED 624 operate. Differences may be found in the resistance values of resistors 635 and 637 and the forward voltage drop across LED 634, as compared to the same counterpart components of LED driving circuitry 620. For example, the forward drop voltage of LED 634 may be greater than the forward drop voltage of LED 624. As result, this may be why the power signal supplied by power bus 610 is boosted for LED 634, but bucked for LED 624. In addition, the output voltage (Vout_Blue) may be different than output voltage of LDO 623. The reference voltage (Vadj_Blue) may be the same as the reference voltage (Vadj_IR) provided to LDO 623.

It should be appreciated that the differences in forward voltages of LEDs 624 and 634 is one of the reasons why two separate LED driving circuits are used to drive LEDs 624 and 634. With the range in supply voltages, it is more efficient to provide custom tailored driving circuits for each LED rather than providing a single power signal for both LEDs. That is, by providing custom power signals for each LED, greater efficiency and reliable operation of the LEDs can be achieved than by powering both LEDs with a common power signal.

In an alternative embodiment, LED driving circuitry 630 can eliminate buck converter 621 and RC filter 622 and have LDO 623 coupled directly to power bus 610 (e.g., a battery).

Figure 7:
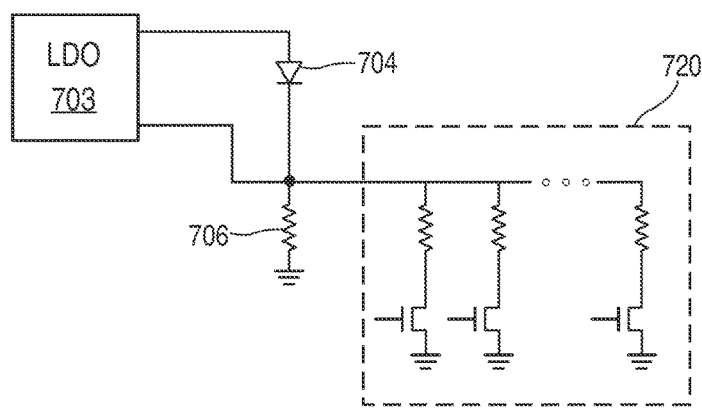
FIG. 7 shows an alternative LDO/LED arrangement in which multiple different current levels can be selected to drive the LED at different brightness levels, according to an embodiment.

FIG. 7 shows an alternative LDO/LED arrangement in which multiple different current levels can be selected to drive the LED at different brightness levels. Such an arrangement may be used in LED driving circuitry 620 and/or 630. FIG. 7 shows LDO 703, LED 704, resistor 707, and current selection circuitry 720. Current selection circuitry 720 can include any number of resistor/switch combinations (three of which are shown). The resistance values can be the same or different. A processor can selectively turn on one or more switches to achieve a desired current draw though LED 704.

Any processes described with respect to FIGS. 1-7, as well as any other aspects of the invention, may each be implemented by software, but may also be implemented in hardware, firmware, or any combination of software, hardware, and firmware. They each may also be embodied as machine- or computer-readable code recorded on a machine- or computer-readable medium. The computer-readable medium may be any data storage device that can store data or instructions that can thereafter be read by a computer system. Examples of the computer-readable medium may include, but are not limited to; read-only memory, random-access memory, flash memory, CD-ROMs, DVDs, magnetic tape, and optical data storage devices. The computer-readable medium can also be distributed over network-coupled computer systems so that the computer readable code is stored and executed in a distributed fashion. For example, the computer-readable medium may be communicated from one electronic subsystem or device to another electronic subsystem or device using any suitable communications protocol. The computer-readable medium may embody computer-readable code, instructions, data structures, program modules, or other data in a modulated data signal, such as a carrier wave or other transport mechanism, and may include any information delivery media. A modulated data signal may be a signal that has one or more of its characteristics set or changed in such a manner as to encode information in the signal.

It is to be understood that any or each module or state machine discussed herein may be provided as a software construct, firmware construct, one or more hardware components, or a combination thereof. For example, any one or more of the state machines or modules may be described in the general context of computer-executable instructions, such as program modules, that may be executed by one or more computers or other devices. Generally, a program module may include one or more routines, programs, objects, components, and/or data structures that may perform one or more particular tasks or that may implement one or more particular abstract data types. It is also to be understood that the number, configuration, functionality, and interconnection of the modules or state machines are merely illustrative, and that the number, configuration, functionality, and interconnection of existing modules may be modified or omitted, additional modules may be added, and the interconnection of certain modules may be altered.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Therefore, reference to the details of the preferred embodiments is not intended to limit their scope.

What is claimed is:

1. A method for powering first and second light emitting diodes (LEDs) in a smoke sensor of a hazard detection system, the system comprising a power source signal ranging between a first signal value and a second signal value, the method comprising:
   managing a first LED power signal for use by the first LED, wherein managing the first LED power signal comprises:
      down converting the power source signal to the first LED power level, wherein the first LED power signal has a value less than the first and second signal values; and
   managing a second LED power signal for use by the second LED, wherein managing the second LED power signal comprises:
      up converting the power source signal to the second LED power signal, wherein the second LED power signal has a value greater than the first and second signal values.

2. The method of claim 1, wherein managing the first LED power signal comprises filtering the first LED power signal with a RC filter to produce a filtered first LED power signal.

3. The method of claim 2, wherein managing the first LED power signal comprises using a first low dropout regulator to supply a substantially constant-current to the first LED, wherein the first low dropout regulator receives the filtered first LED power signal.

4. The method of claim 2, wherein the first LED is characterized by a first forward voltage drop, wherein the first dropout regulator is characterized a first LDO feedback voltage, and wherein the first LED power signal exceeds the summation of the first forward voltage drop and the first LDO feedback voltage.

5. The method of claim 2, further comprising:
   supplying the first LED power signal to at least one circuit other than the first LED.

6. The method of claim 5, further comprising:
   driving the first LED according to a known pulse profile, where the RC filter is tuned based on the known pulse profile to ensure that a simultaneous load demand of the at least one circuit and the first LED does not exceed a maximum current output of the power source signal.

7. The method of claim 1, wherein managing a second LED power signal comprises using a second low dropout regulator to supply a substantially constant-current to the second LED, wherein the second low dropout regulator receives the second LED power signal.

8. The method of claim 7, wherein the second LED is characterized by a second forward voltage drop, wherein the second dropout regulator is characterized a second LDO feedback voltage, and wherein the second LED power signal exceeds the summation of the second forward voltage drop and the second LDO feedback voltage.

9. The method of claim 1, further comprising:
   selectively activating the first LED with the first LED power signal;
   monitoring for scattered electromagnetic energy derived from electromagnetic energy being emitted by the selectively activated first LED;
   selectively activating the second LED with the second LED power signal; and
   monitoring for scattered electromagnetic energy derived from electromagnetic energy being emitted by the selectively activated second LED.

10. A hazard detection system, comprising:
   a smoke chamber comprising first and second light emitting diodes (LEDs);
   a power input configured to receive a power signal ranging between first and second values;

first LED driving circuitry coupled to receive the power signal from the power input and operative to provide a first LED power signal to the first LED, the first LED power signal characterized as having a value lower than the first and second values and a first substantially constant current value; and second LED driving circuitry coupled to receive the power signal from the power input and operative to provide a second LED power signal to the second LED, the second LED power signal characterized as having a value higher than the first and second values and a second substantially constant current.

11. The hazard detection system of claim 10, wherein the first LED driving circuitry comprises:

a buck converter coupled to the power input and operative to generate the first LED power signal;

an RC filter coupled to the buck converter and operative to filter the first LED power signal;

a first low dropout regulator coupled to the RC filter and both terminals of the first LED, the first low dropout regulator operative to provide the first substantially constant current value to the first LED; and a current setting resistor coupled to the first low dropout regulator and the first LED.

12. The hazard detection system of claim 11, further comprising:

wireless circuitry coupled to the buck converter and powered by the first power signal, wherein the RC filter sets a ceiling on current draw from the power input when the wireless circuitry and first LED are simultaneously operating.

13. The hazard detection system of claim 10, wherein the second LED driving circuitry comprises:

a boost converter coupled to the power input and operative to generate the second LED power signal;

a second low dropout regulator coupled to the boost converter and both terminals of the second LED, the second low dropout regulator operative to provide the second substantially constant current value to the second LED; and a current setting resistor coupled to the second low dropout regulator and the second LED.

14. The hazard detection system of claim 13, further comprising:

a speaker coupled to the boost converter and operative to be powered by the second LED power signal.

15. The hazard detection system of claim 10, wherein the smoke chamber further comprises at least one energy detector, the system further comprising a processor operative to:

selectively activate the first LED with the first LED power signal;

monitor the at least one energy detector for scattered electromagnetic energy derived from electromagnetic energy being emitted by the selectively activated first LED;

selectively activate the second LED with the second LED power signal; and monitor the at least one energy detector for scattered electromagnetic energy derived from electromagnetic energy being emitted by the selectively activated second LED.

16. The hazard detection system of claim 10, wherein the first LED is an infrared LED, and where the second LED is a blue LED.

17. The hazard detection system of claim 10, wherein the power input is coupled to a battery, and wherein the first LED driving circuitry further comprises:

a first low dropout regulator coupled to the battery and both terminals of the first LED, the first low dropout regulator operative to provide the first substantially constant current value to the first LED; and a current setting resistor coupled to the first low dropout regulator and the first LED.

18. The hazard detection system of claim 17, further comprising: wireless circuitry coupled to the battery and powered by the first power signal, wherein the RC filter sets a ceiling on current draw from the power input when the wireless circuitry and first LED are simultaneously operating.

19. A particle detector for use in a hazard detection system that is powered by one of a plurality of different power sources, wherein a power signal supplied by the plurality of power source ranges between first and second values, the particle detector comprising:

a particle detection chamber comprising an infrared light emitting diode (IR LED), a blue light emitting diode (LED), and a photodetector;

a power input for receiving the power signal; and

LED driving circuitry coupled to the IR LED, the blue LED, and to receive the power signal, the LED driving circuitry operative to supply a first drive current to the IR LED and a second drive current to the blue LED, wherein the first and second drive currents are independently derived from the power signal using independently operating low dropout regulators.

20. The particle detector of claim 19, wherein the first and second drive currents are maintained as relatively constant currents when the power signal ranges between the first and second values.

21. The particle detector of claim 19, wherein the low dropout regulator associated with the blue LED requires a boosted power signal that exceeds the first and second values in order to operate.

22. The particle detector of claim 19, wherein the low dropout regulator associated with the IR LED requires a power signal that falls below the first and second values in order to operate most efficiently.

* * * * *